(12) United States Patent
Kealey et al.

(10) Patent No.: US 11,690,632 B2
(45) Date of Patent: *Jul. 4, 2023

(54) INTRASACCULAR THIN-FILM FLOW DIVERTERS AND RELATED METHODS

(71) Applicant: Monarch Biosciences, Inc., Los Angeles, CA (US)

(72) Inventors: Colin Kealey, Los Angeles, CA (US); Vikas Gupta, Los Angeles, CA (US)

(73) Assignee: MONARCH BIOSCIENCES, INC., Los Angeles, CA (US)

(*) Notice: Subject to any disclaimer, the term of this patent is extended or adjusted under 35 U.S.C. 154(b) by 252 days.

This patent is subject to a terminal disclaimer.

(21) Appl. No.: 17/146,345

(22) Filed: Jan. 11, 2021

(65) Prior Publication Data
US 2021/0128166 A1 May 6, 2021

Related U.S. Application Data
(63) Continuation of application No. 16/010,341, filed on Jun. 15, 2018, now Pat. No. 10,888,333, which is a
(Continued)

(51) Int. Cl.
*A61B 17/12* (2006.01)
*A61B 17/00* (2006.01)

(52) U.S. Cl.
CPC .. *A61B 17/12172* (2013.01); *A61B 17/12113* (2013.01); *A61B 17/12163* (2013.01);
(Continued)

(58) Field of Classification Search
CPC ........ A61B 17/12172; A61B 17/12113; A61B 17/12163; A61B 2017/00526; A61B 2017/00596; A61B 2017/00632
See application file for complete search history.

(56) References Cited

U.S. PATENT DOCUMENTS

| | | | |
|---|---|---|---|
| 5,800,393 | A | 9/1998 | Sahota |
| 6,093,199 | A | 7/2000 | Brown et al. |

(Continued)

FOREIGN PATENT DOCUMENTS

| | | |
|---|---|---|
| WO | WO 99/12484 | 3/1999 |
| WO | WO 2016/210380 | 12/2016 |
| WO | WO 2017/004598 | 1/2017 |

*Primary Examiner* — Tuan V Nguyen
(74) *Attorney, Agent, or Firm* — Haynes and Boone, LLP

(57) ABSTRACT

An intrasaccular flow diverter includes a wire structure (e.g., a braided wire or a laser-cut hypotube), a thin-film mesh placed over the wire structure, and crimps fixing the thin-film mesh to the wire structure at each crimp. The wire structure and the thin-film mesh between adjacent crimps are expanded radially to form thin-film covered spheroid structures. When deployed in an aneurysm, the spheroid structures may volumetrically fill the aneurysm sac. An intrasaccular flow diverter with an umbrella structure includes a wire structure with a plurality of crimps along the wire structure, and a thin-film covered umbrella structure at one end of the wire structure. The wire structure between adjacent crimps is expanded radially to form a spheroid structure. When deployed in an aneurysm, the thin-film covered umbrella structure may cover the aneurysm neck.

20 Claims, 21 Drawing Sheets

Related U.S. Application Data continuation of application No. PCT/US2016/067038, filed on Dec. 15, 2016.

(60) Provisional application No. 62/267,837, filed on Dec. 15, 2015.

(52) U.S. Cl.
CPC ............ *A61B 2017/00526* (2013.01); *A61B 2017/00592* (2013.01); *A61B 2017/00606* (2013.01); *A61B 2017/00641* (2013.01); *A61B 2017/00867* (2013.01); *A61B 2017/1205* (2013.01)

(56) References Cited

U.S. PATENT DOCUMENTS

| | | |
|---|---|---|
| 8,672,990 B2 | 3/2014 | Holman et al. |
| 10,888,333 B2 | 1/2021 | Kealey et al. |
| 2002/0111647 A1 | 8/2002 | Khairkhahan |
| 2005/0261758 A1 | 11/2005 | Rourke et al. |
| 2007/0255388 A1 | 11/2007 | Rudakov et al. |
| 2008/0004653 A1 | 1/2008 | Sherman |
| 2008/0161936 A1 | 7/2008 | Feller |
| 2011/0196413 A1* | 8/2011 | Wallace ............ A61B 17/12172 606/194 |
| 2013/0325053 A1 | 12/2013 | Porter et al. |
| 2014/0135812 A1 | 5/2014 | Divino |
| 2014/0249620 A1 | 9/2014 | Carman et al. |
| 2014/0330299 A1* | 11/2014 | Rosenbluth ...... A61B 17/12154 606/191 |
| 2015/0173770 A1 | 6/2015 | Warner |
| 2017/0079662 A1 | 3/2017 | Rhee |
| 2018/0296224 A1 | 10/2018 | Kealey et al. |

\* cited by examiner

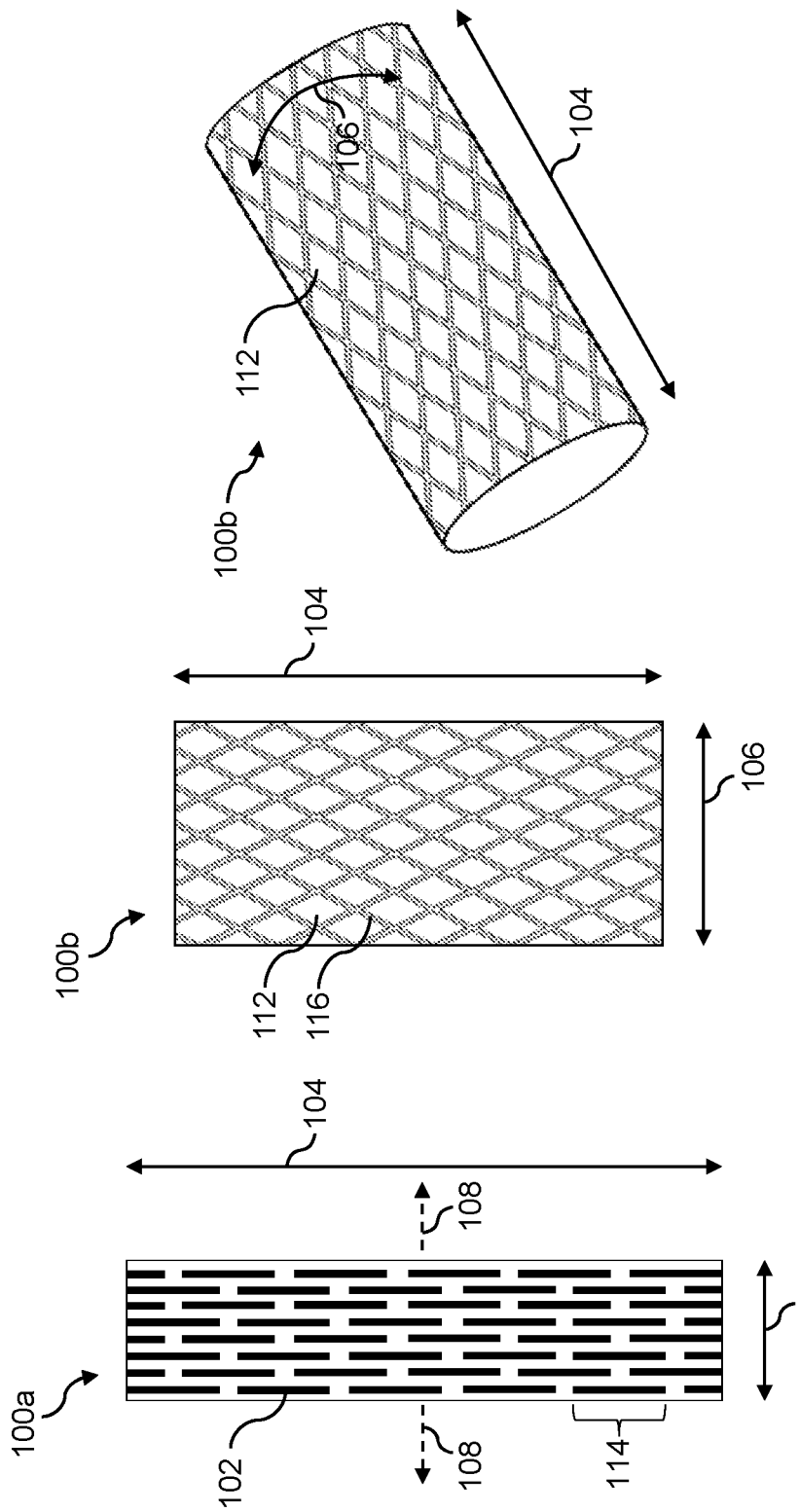

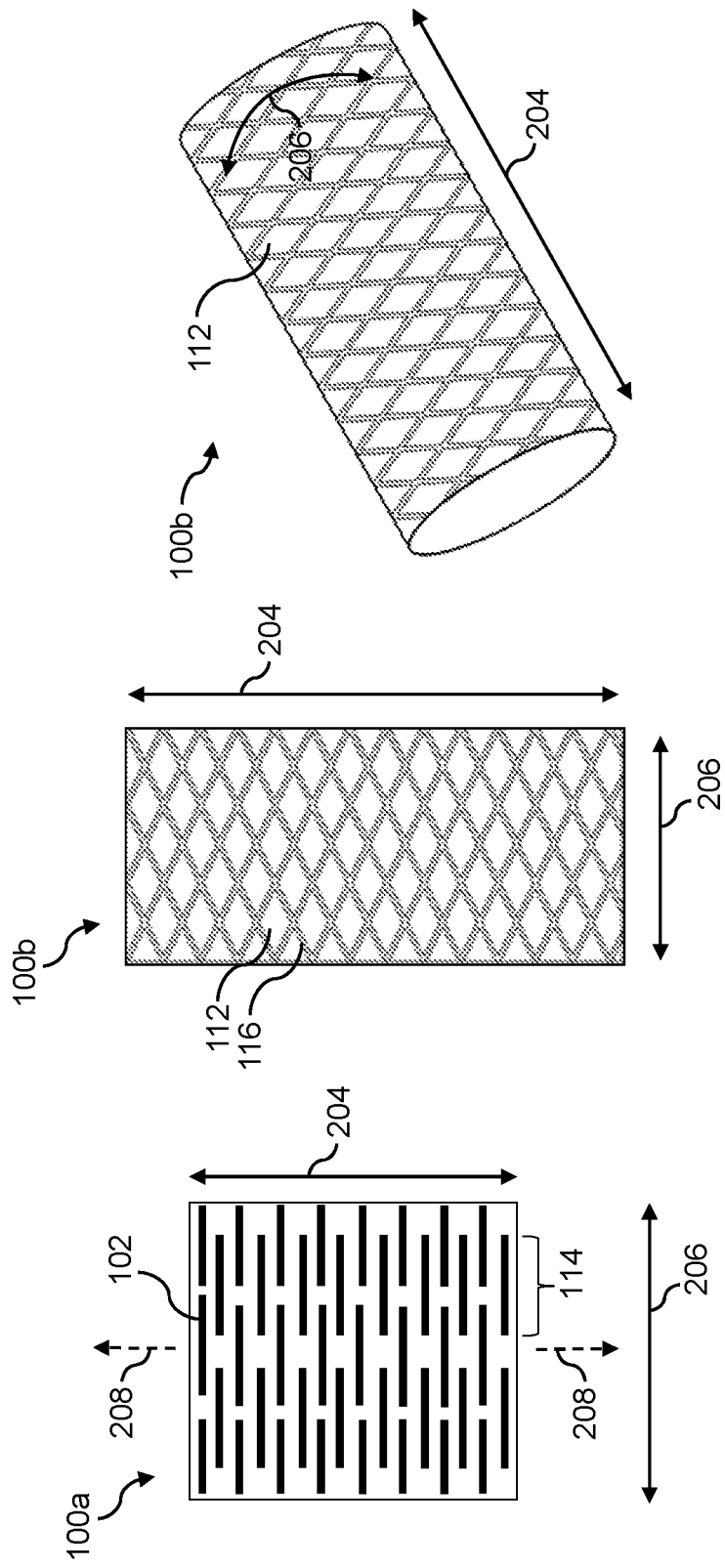

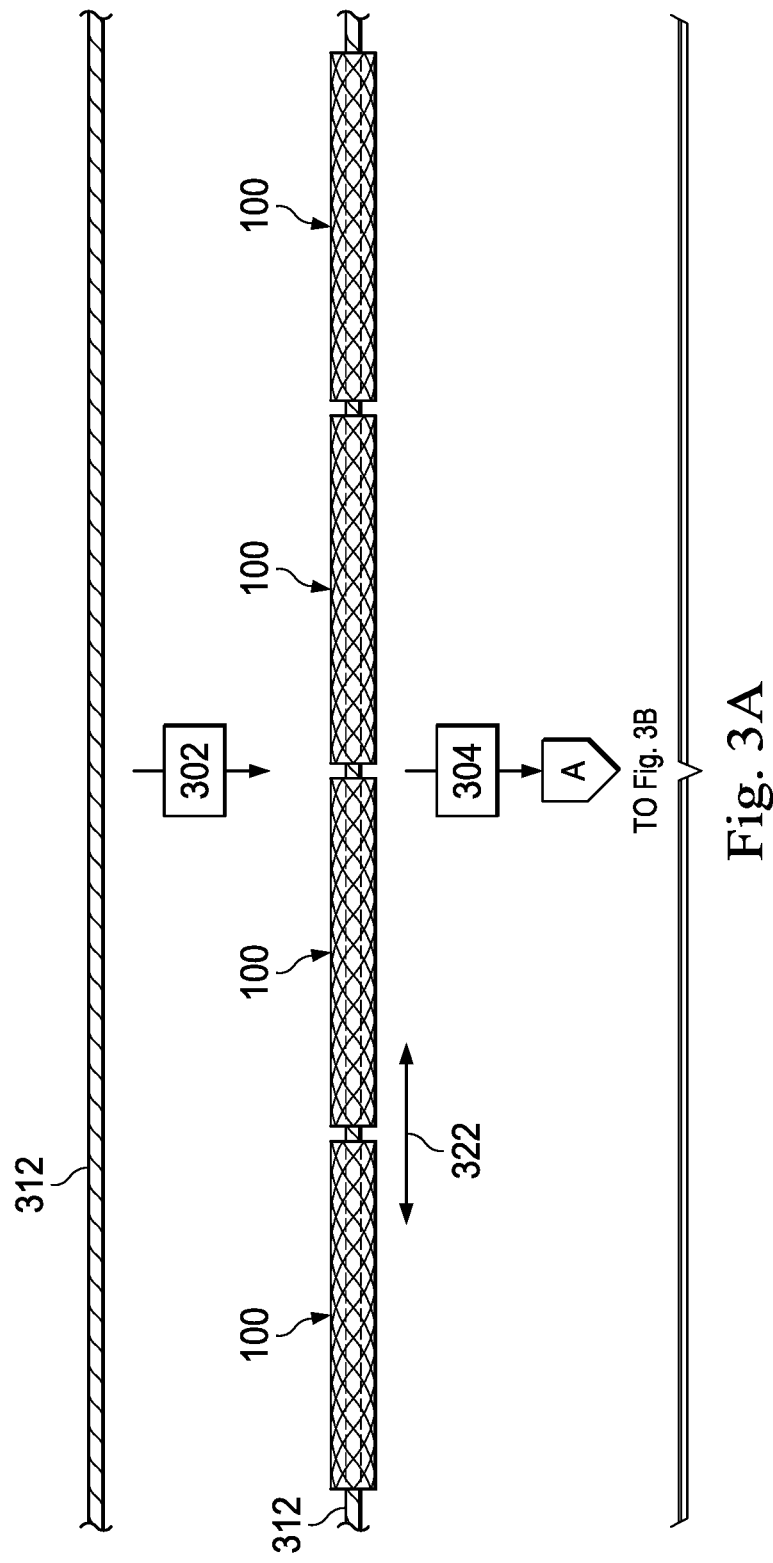

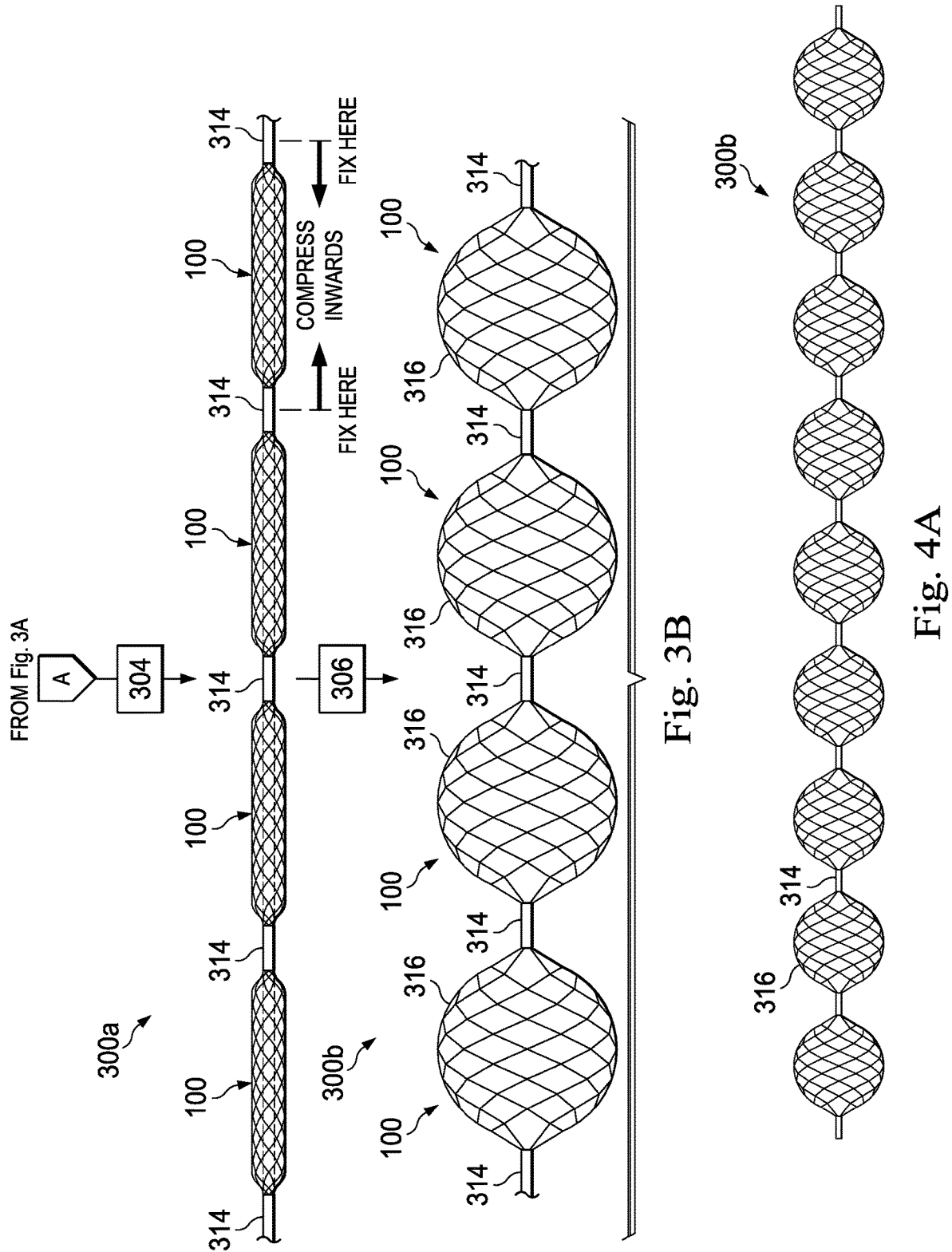

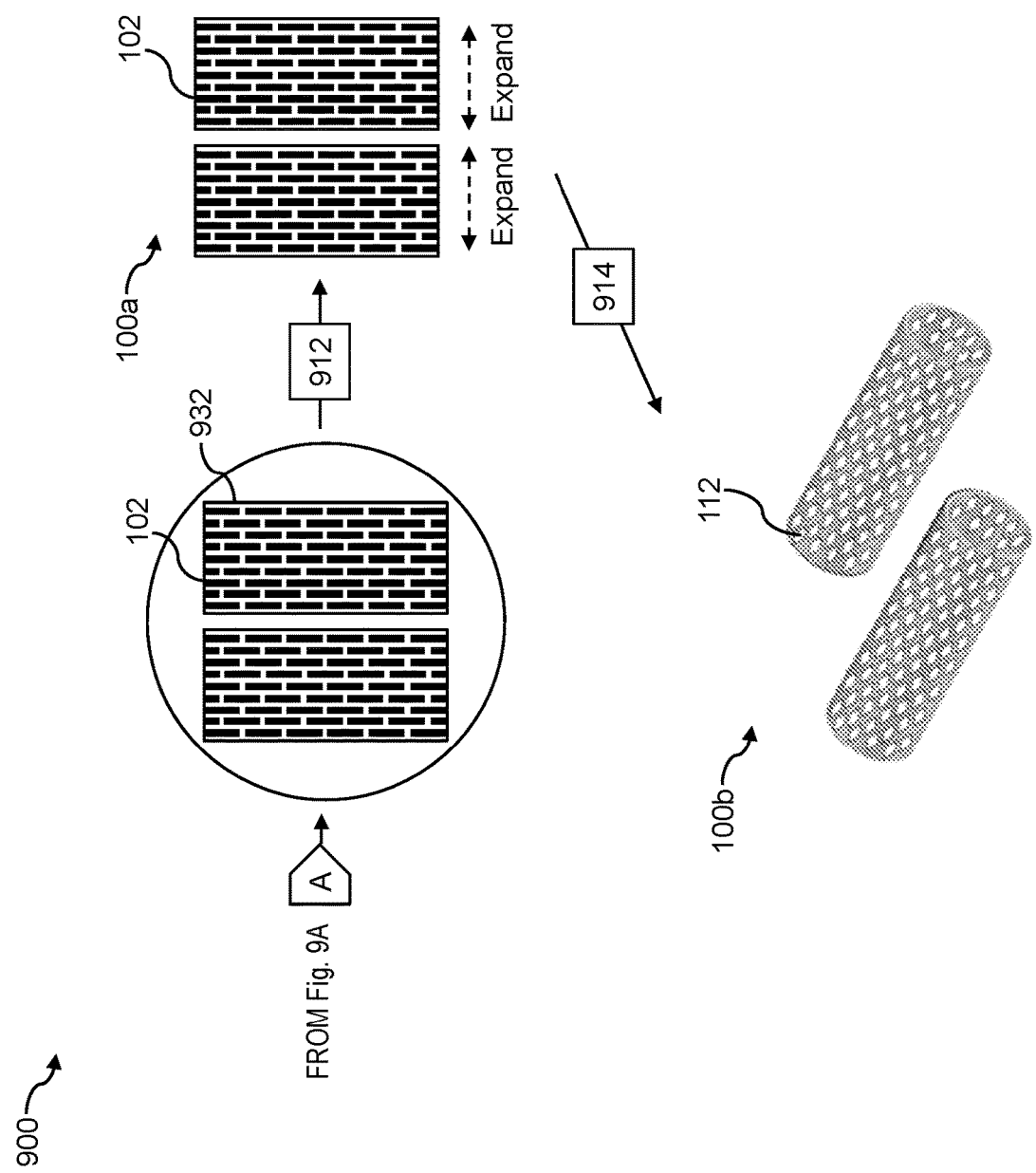

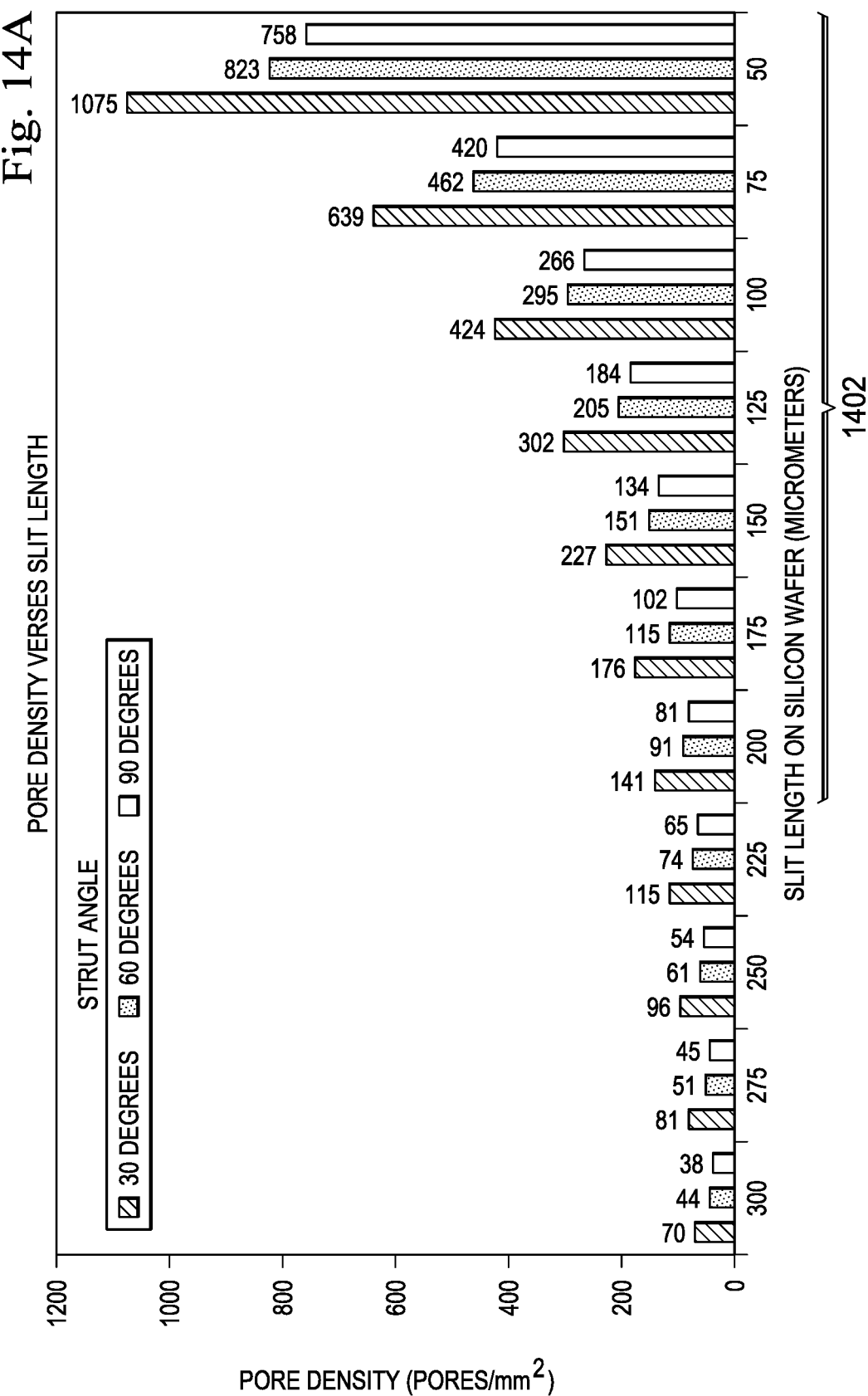

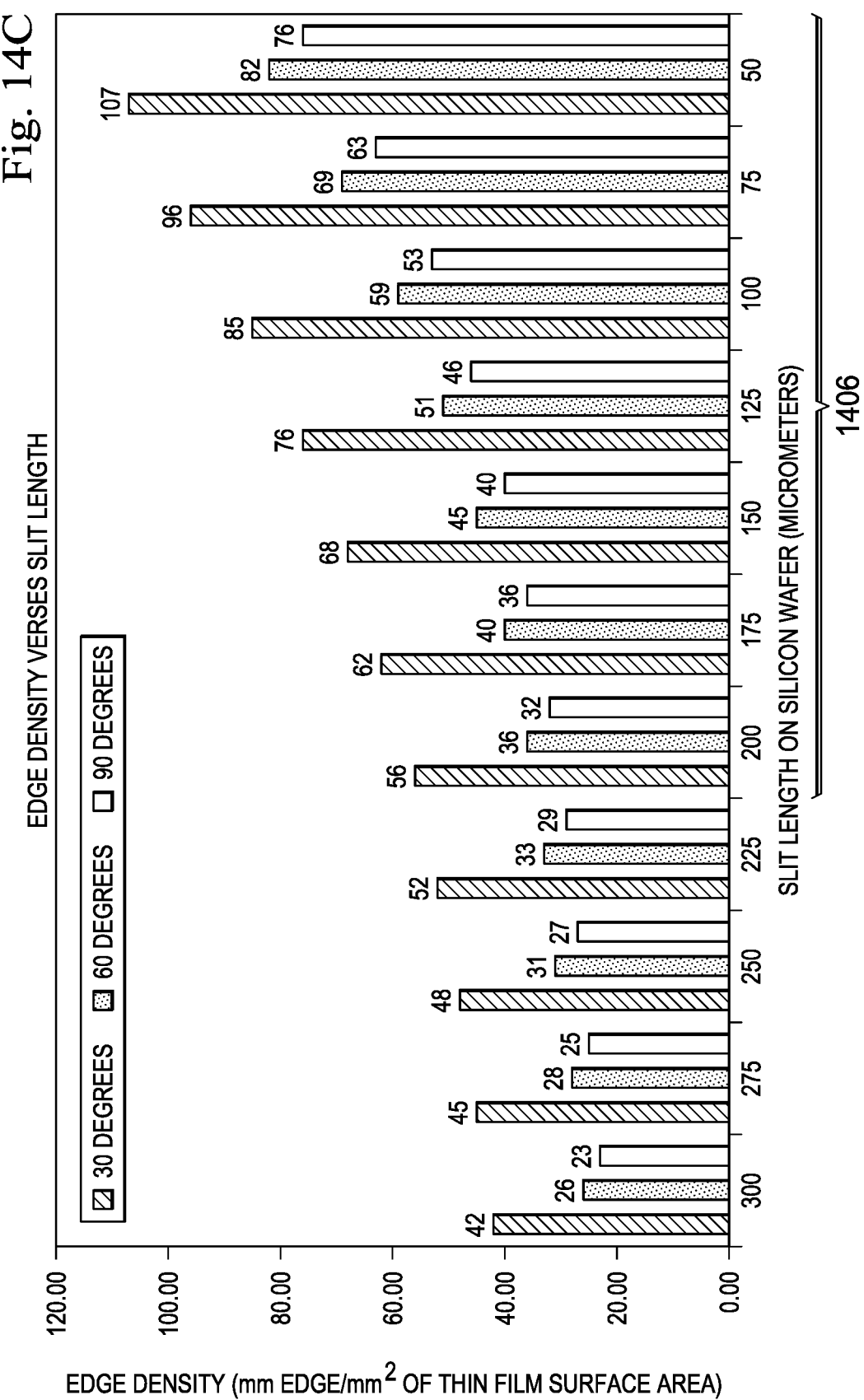

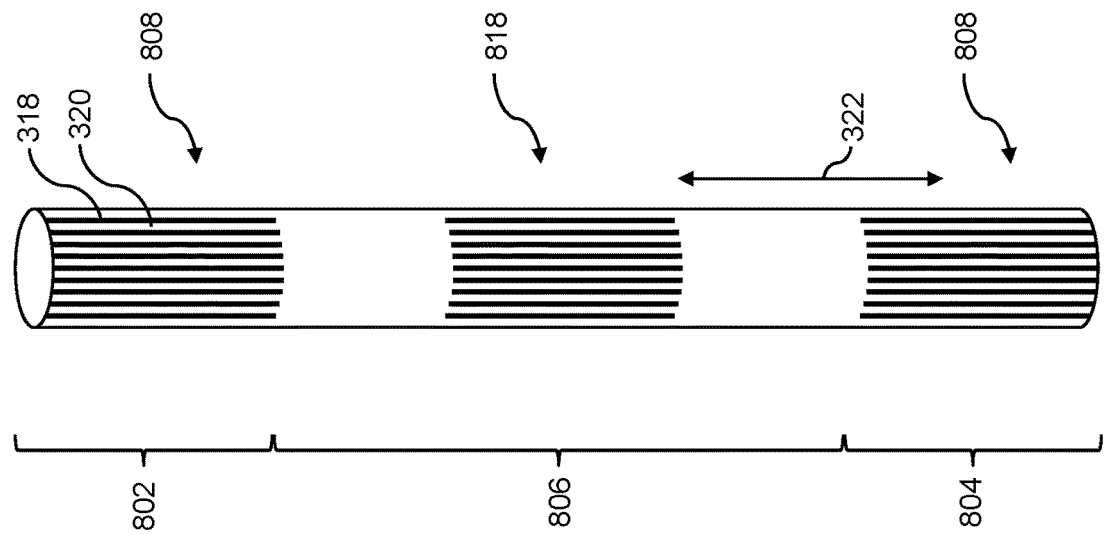
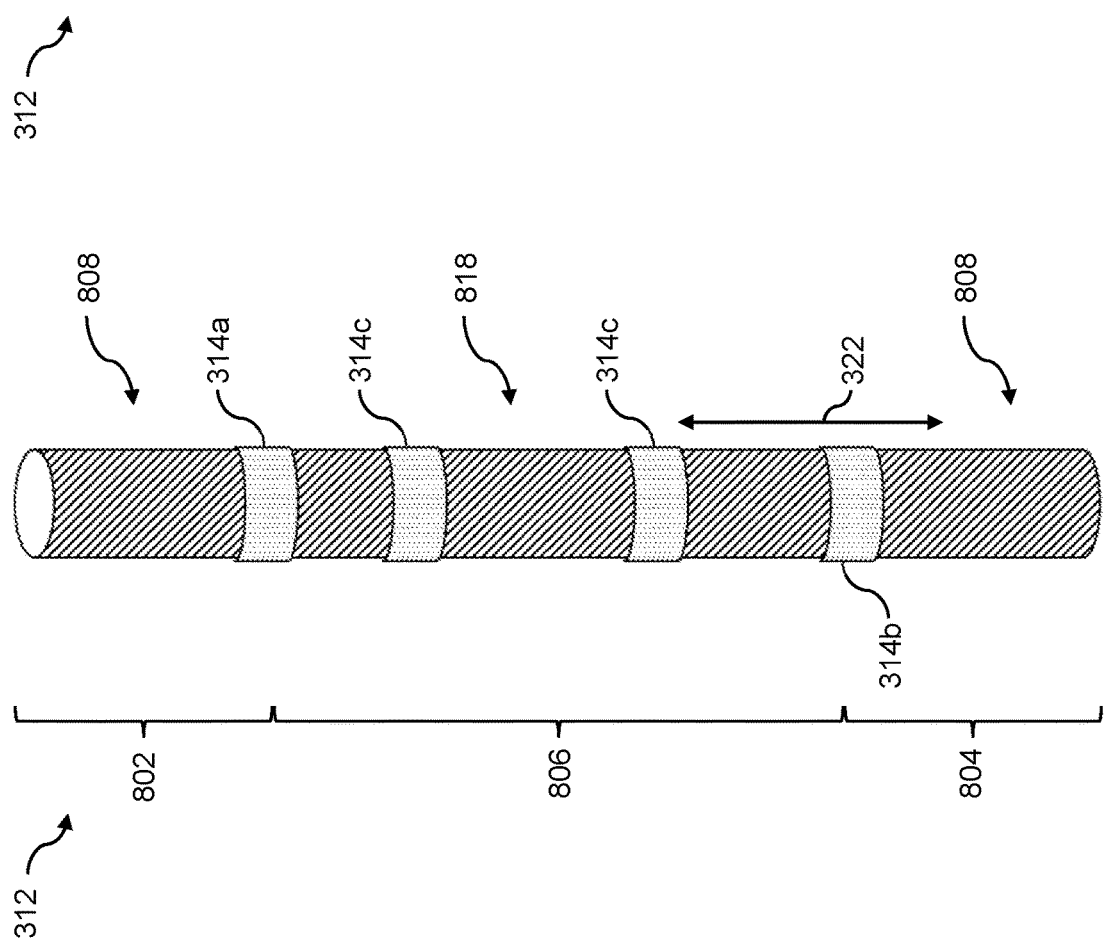

INTRASACCULAR THIN-FILM FLOW DIVERTERS AND RELATED METHODS

CROSS-REFERENCE TO RELATED APPLICATIONS

The present application is a continuation application of U.S. patent application Ser. No. 16/010,341, filed on Jun. 15, 2018, which is a continuation of International Application No. PCT/US2016/067038, filed on Dec. 15, 2016, which claims the benefit of U.S. Provisional Application No. 62/267,837, filed on Dec. 15, 2015, which are all hereby incorporated by reference in their entirety.

TECHNICAL FIELD

The present disclosure relates to medical devices and, more particularly, to intrasaccular flow diverters.

BACKGROUND

Tissue defects may involve an absence of healthy tissue in a body area where such tissue would normally be present. For example, common tissue defects include arterial or venous aneurysms, in which a defect in a blood vessel wall causes an outpouching of the vessel tissue. Other common tissue defects include arteriovenous fistulas, intestinal fistulas, colonic fistulas, anal fistulas, hernias, and traumatic wounds.

Coil embolization techniques have been developed to treat aneurysms. A wire is delivered to a sac of an aneurysm and coiled inside the sac. The coiled wire packs the sac densely to limit blood flow into the sac and induces a clot in the sac. However, such coil embolization techniques can only be used for aneurysms with a narrow neck region to hold the coil in place. Further, coil embolization techniques suffer from complications including the risk of recanalization, in which blood flow returns to the sac and further swells the sac.

Covered stents have also been developed to treat aneurysms. A covered stent is placed in a blood vessel such that the covered stent spans a neck region of an aneurysm, thereby diverting blood flow away from a sac of the aneurysm. The stagnant blood inside the aneurysm sac may then clot and the aneurysm may heal. Covered stents, however, also suffer from complications. The most commonly used materials for covered stents include polytetrafluorethylene (PTFE) and polyethylene terephthalate (PET). Both of these materials add substantial bulk, making the stent unsuitable for use in certain vascular beds, such as the neurovasculature. In addition, these materials tend to be impermeable or only semi-permeable. This limits tissue in-growth into the stent covering and leaves a foreign body that is continuously exposed to blood. Because of this, there is a long-term risk of acute thrombosis and stenosis inside the stent. Moreover, because these stents are impermeable to blood flow they will cut-off blood flow to any vessels adjacent to the aneurysm that are covered with the stent. In the neurovasculature, this can lead to unwanted ischemic strokes. In other vascular beds, this can lead to ischemia of critical tissues such as the intestine. Further, blood clots formed at the coil embolization site or covered stent implanted site may dislodge and cause a heart attack, stroke, or other life threatening complications.

Accordingly, there is a need in the art for improved flow diverters and aneurysm treatments.

SUMMARY

The present disclosure is directed to intravascular flow diverters and methods for fabricating intravascular flow diverters. In one embodiment, an apparatus comprises a wire structure comprising a plurality of wires and a plurality of crimps provided along the wire structure at corresponding crimp locations, wherein a respective part of the wire structure between two adjacent crimps is configured to expand radially to form a spheroid structure. In some embodiments, the apparatus includes a thin-film mesh placed over a length of the wire structure, wherein the plurality of crimps are configured to secure the thin-film mesh to the wire structure at corresponding crimped locations, wherein the respective part of the wire structure and a respective part of the thin-film mesh between the two adjacent crimps are configured to expand radially to form the spheroid structure covered with the respective part of the thin-film mesh, and wherein at least expanded parts of the thin-film mesh comprises pores. In some embodiments, the apparatus comprises an umbrella structure at one end of the wire structure comprising umbrella struts. The umbrella structure may include a thin-film sheet attached to the umbrella struts. Further, the apparatus may include another umbrella structure at the other end of the wire structure. The wire structure may comprise a braided wire or a laser-cut hypotube. Also, the umbrella structure(s) may comprise a braided wire or a laser-cut hypotube.

In other embodiments, a method for forming an intrasaccular flow diverter comprises placing a thin-film mesh over a part of a wire structure, attaching the thin-film mesh to the wire structure at a plurality of locations along the wire structure by crimping the thin-film mesh at the plurality of locations to form an intrasaccular flow diverter, expanding the wire structure and the thin-film mesh between each of the crimp locations radially to form a corresponding thin-film covered spheroid structure by compressing the wire structure along a longitudinal axis of the wire structure, and shape setting the intrasaccular flow diverter. In some embodiments, the method further includes forming an umbrella structure at one end of the wire structure (e.g., forming an umbrella structure from an end portion of the wire structure or attaching an umbrella structure at one end of the wire structure). Another umbrella structure may be formed at the other end of the wire structure. The umbrella structure(s) may be formed by forming umbrella struts and attaching a thin-film mesh on the umbrella struts.

BRIEF DESCRIPTION OF THE DRAWINGS

FIG. 1A is a diagrammatic top plan view of a thin-film mesh prior to expansion according to an embodiment of the present disclosure.

FIG. 1B is a diagrammatic top plan view of the thin-film mesh of FIG. 1A after expansion.

FIG. 1C is a diagrammatic perspective view of the thin-film mesh of FIG. 1A after expansion.

FIG. 2A is a diagrammatic top plan view of a thin-film mesh prior to expansion according to an embodiment of the present disclosure.

FIG. 2B is a diagrammatic top plan view of the thin-film mesh of FIG. 2A after expansion.

FIG. 2C is a diagrammatic perspective view of the thin-film mesh of FIG. 2A after expansion.

FIGS. 3A and 3B illustrate a process of forming an intrasaccular flow diverter according to an embodiment of the present disclosure.

FIGS. 4A, 4B, and 4C illustrate a process of setting a shape of an intrasaccular flow diverter according to an embodiment of the present disclosure.

FIGS. 9A and 9B illustrate a process of fabricating thin-film meshes for a thin-film device according to an embodiment of the present disclosure.

FIGS. 14A, 14B, and 14C are graphs characterizing thin-film meshes when one or more features are varied according to various embodiments of the present disclosure.

FIG. 16A is a diagrammatic perspective view of a braided wire for an intrasaccular flow diverter with a central spring according to an embodiment of the present disclosure.

FIG. 16B is a diagrammatic perspective view of a hypotube structure for an intrasaccular flow diverter with a central spring according to an embodiment of the present disclosure.

Figure 4B:
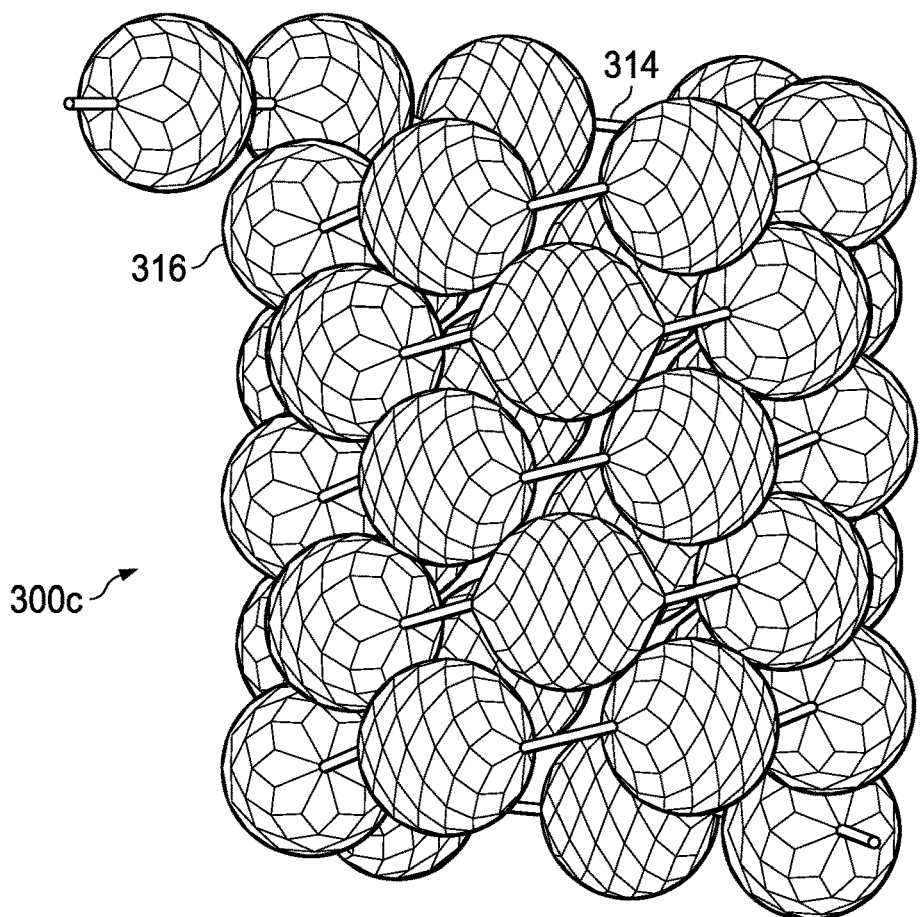

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

Intrasaccular flow diverters that include thin-film meshes (also referred to as intrasaccular thin-film flow diverters) and related methods are provided. The thin-film mesh is composed of a metallic material or a pseudometallic material. For example, the thin-film mesh may be a thin-film Nitinol (TFN) mesh composed of Nitinol (i.e., Nickel Titanium).

A thin-film mesh composed of metallic material provides a number of advantages compared to a thin-film mesh composed of polymeric material, which is commonly used for covered stent grafts, hernia repair, and fistulae. Thin-film meshes composed of metallic material facilitate more robust cellular adhesion and tissue incorporation compared to meshes composed of polymeric material because thin-film meshes composed of metallic material are much thinner and have a well-defined porosity as compared to polymeric mesh materials. Further, thin-film meshes composed of metallic material may be superior for long term implants because implantation of polymeric biomaterials tends to elicit a greater inflammatory response than metallic biomaterials.

Thin-film meshes may be formed using sputter deposition and lift-off techniques and micropatterned silicon wafers such that the composition, thickness, and pattern of the thin-film meshes are controlled at the micrometer and/or nanometer level. For example, a silicon wafer is patterned with a series of grooves using deep reactive ion etching (DRIE). The resolution of micropatterns formed using DRIE may be approximately 1 μm (micrometers, or microns). The term "approximately," as used herein when referring to a measurable value, encompasses variations of ±20%, ±10%, ±5%, ±1%, ±0.5%, or ±0.1% of the value. A thin-film mesh is formed by sputter deposition of Nitinol onto the silicon wafer. The pattern of grooves are reproduced in the thin-film mesh as a corresponding pattern of slits. The slits have a length (along its long dimension) that is significantly greater than their width, so the fabricated thin-film mesh is capable of significant expansion on the order of 25% to 800% from its original fabricated length as the slits are opened up to assume diamond-shaped pore/fenestration configuration.

The dimensions of the diamond-shaped pores can be precisely controlled during fabrication and expansion of the thin-film mesh such that the diamond-shaped pores have dimensions that facilitate healing of a tissue defect. During fabrication and expansion, features such as the percentage of surface area covered by the thin-film mesh (i.e., 1—porosity), the pore density (i.e., the number of pores per $mm^2$ of mesh surface area), the edge density (i.e. total length of pore edges per $mm^2$ of surface area), and the pore geometry may be determined. The thin-film mesh may be formed as a stand-alone intrasaccular flow diverter or may be combined with one or more other structural components (e.g., a structural backbone, a braided wire, or other structural component) to form an intrasaccular flow diverter.

FIGS. 1A, 1B, and 1C illustrate a thin-film mesh 100 prior to expansion (thin-film mesh 100a in FIG. 1A) and after expansion (thin-film mesh 100b in FIGS. 1B and 1C). FIG. 1A is a diagrammatic top plan view of thin-film mesh 100a prior to expansion. Thin-film mesh 100a forms a series of micropatterned slits 102 (e.g., closed fenestrations). Thin-film mesh 100a has a long axis 104 and a short axis 106. Slits 102 are oriented parallel or substantially parallel (e.g., oriented at an angle between 0 degrees and 30 degrees) to axis 104, also referred to as the slit axis 104. Accordingly, slits 102 are oriented perpendicular or substantially perpendicular (e.g., oriented at an angle between 60 degrees and 90 degrees) to axis 106. Thin-film mesh 100a may be expanded by extending thin-film mesh 100a in directions 108 along axis 106, also referred to as the axis of expansion 106, to form expanded thin-film mesh 100b of FIGS. 1B and 1C, in which slits 102 have opened up to form a series of diamond-shaped pores 112.

Slit length 114 may be modulated based on the type of medical treatment, the body region being treated, and/or the type of aneurysm being treated. Further, the ability of thin-film mesh 100a to effectively expand along axis 106 depends on the length of slits 102. Slits 102 with a longer slit length will result in thin-film mesh 100a with increased ability for expansion, while slits 102 with a shorter slit length will result in thin-film mesh 100a with a decreased ability for expansion. Each of slits 102 may have slit length 114 (length along axis 104) of between 50 μm and 500 μm. Thin-film mesh 100a fabricated with slit length 114 of between 50 μm and 200 μm advantageously facilitates reconstruction of tissue defects that are superior to other slit lengths, such as by promoting rapid fibrin deposition and cell growth (e.g., endothelialization) when placed in a blood vessel.

In some embodiments, thin-film mesh 100a is fabricated as two layers of thin-film on a silicon wafer using silicon wafer micromachining technology, as described below in relation to FIGS. 9A and 9B. As the two layers of thin-film are stacked, only the top layer is visible in FIG. 1A, and the two layers of thin-film may be joined at the two edges along axis 104. In some embodiments, a bonding metal is deposited at the longitudinal edge between the two layers such that heating of the construct to the bonding metal's melting temperature results in fusion of the two layers to form a seam.

FIG. 1B is a diagrammatic top plan view of thin-film mesh 100b formed by expanding thin-film mesh 100a of FIG. 1A. Thin-film mesh 100b forms a plurality of diamond-shaped pores 112 (e.g., open fenestrations). The expansion may extend thin-film mesh 100a along axis 106 such that there is a large increase in width (length along axis 106) but a small decrease in longitudinal length (length along axis 104). In some embodiments, the expansion may extend thin-film mesh 100a along axis 104 in a range from 25% to 800%.

When thin-film mesh 100a of FIG. 1A is expanded to thin-film mesh 100b, slits 102 of thin-film mesh 100a open up to pores/fenestrations 112 to form a "chain-link" fence pattern, such as diamond-shaped pores/fenestrations. Thin-film mesh 100b forms struts 116 around each diamond-shaped pore/fenestration 112. It will be appreciated that other pore/fenestration shapes may be used in alternative embodiments. The diamond shape of each pore 112 may be longer along axis 104, also referred to as long diagonal axis 104 of diamond-shaped pore 112, and shorter along axis 106, also referred to as the short diagonal axis 106 of diamond-shaped pore 112.

FIG. 1C is a diagrammatic perspective view of thin-film mesh 100b formed by expanding thin-film mesh 100a of FIG. 1A. As shown in FIG. 1C, thin-film mesh 100b has a three-dimensional cylindrical shape. Cylindrical thin-film mesh 100b may be used, for example, as a thin-film mesh covering at least a part of an intrasaccular flow diverter, as shown in FIG. 3. Other three-dimensional shapes may be formed in other embodiments.

The pore density and the percent metal coverage (PMC) may be modulated based on the type of medical treatment, the body region being treated, and/or the type of aneurysm being treated. Thin-film mesh 100a may be fabricated with slit length 114 of between 50 μm and 500 μm and expanded to thin-film mesh 100b having a pore density (fenestrations per square mm) of between 15 pores/mm$^2$ and 2217 pores/mm$^2$ and a percent metal coverage of between 6% and 83%, as described in further detail below in relation to FIGS. 11A and 11B and FIGS. 12A and 12B. Thin-film mesh 100a fabricated with slit length 114 of between 50 μm and 200 μm and expanded to thin-film mesh 100b having a high pore density of between 81 pores/mm$^2$ and 1075 pores/mm$^2$ and a low metal coverage of between 19% and 66% advantageously facilitates reconstruction of tissue defects that are superior to other pore densities/percent metal coverage, such as by promoting a planar deposition of fibrin followed by rapid cell growth (e.g., endothelialization) when placed in a blood vessel.

FIGS. 2A, 2B, and 2C illustrate a thin-film mesh 100 prior to expansion (thin-film mesh 100a in FIG. 2A) and after expansion (thin-film mesh 100b in FIGS. 2B and 2C). FIG. 2A is a diagrammatic top plan view of thin-film mesh 100a prior to expansion. Thin-film mesh 100a forms a series of micropatterned slits 102 (e.g., closed fenestrations). Thin-film mesh 100a has a long axis 204 and a short axis 206. Slits 102 are oriented parallel or substantially parallel (e.g., oriented at an angle between 0 degrees and 30 degrees) to axis 206, also referred to as the slit axis 206. Accordingly, slits 102 are oriented perpendicular or substantially perpendicular (e.g., oriented at an angle between 60 degrees and 90 degrees) to axis 204. Thin-film mesh 100a may be expanded by extending thin-film mesh 100a in directions 208 along axis 204, also referred to as the axis of expansion 204, to form an expanded thin-film mesh 100b of FIGS. 2B and 2C, in which slits 102 have opened up to form a series of diamond-shaped pores 112.

Slit length 114 may be modulated based on the type of medical treatment, the body region being treated, and/or the type of aneurysm being treated. Further, the ability of thin-film mesh 100 to effectively expand along axis 204 may depend on the length of slits 102. Slits 102 with a longer slit length will result in thin-film mesh 100 with increased ability for expansion, while slits 102 with a shorter slit length will result in thin-film mesh 100 with a decreased ability for expansion. Each of slits 102 may have slit length 114 (length along axis 206) of between 50 and 500 μm. Thin-film mesh 100 fabricated with slit length 114 of between 50 μm and 200 μm advantageously facilitates reconstruction of tissue defects that are superior to other slit lengths 114, such as by promoting rapid fibrin deposition and cell growth (e.g., endothelialization) when placed in a blood vessel.

In some embodiments, thin-film mesh 100a is fabricated as two layers of thin-film on a silicon wafer using silicon wafer micromachining technology, as described below in relation to FIGS. 9A and 9B. As the two layers of thin-film are stacked, only the top layer is visible in FIG. 2A, and the two layers of thin-film may be joined at the two edges along axis 204. In some embodiments, a bonding metal is deposited at the longitudinal edge between the two layers such that heating of the construct to the bonding metal's melting temperature results in fusion of the two layers to form a seam.

Each of the two layers of thin-film mesh 100a may have a width (length along axis 206) that is approximately half of the circumference of the final device, such as thin-film mesh 100b expanded to its three-dimensional form (e.g., a cylindrical tube) as shown in FIG. 2C. Accordingly, cylindrical thin-film mesh 100b may have a circumference that is approximately twice or slightly less than twice of the width of thin-film mesh 100a. For example, if thin-film mesh 100a is 4 mm wide, cylindrical thin-film mesh 100b may have a circumference of 7.4 mm and a diameter of 2.4 mm.

FIG. 2B is a diagrammatic top plan view of thin-film mesh 100b formed by expanding thin-film mesh 100a of FIG. 2A. Thin-film mesh 100b forms a plurality of diamond-shaped pores 112 (e.g., open fenestrations). The expansion may extend thin-film mesh 100a along axis 204 such that there is a large increase in longitudinal length (length along axis 204) but a small decrease in width (length along axis 206). In some embodiments, the expansion may longitudinally extend thin-film mesh 100a along axis 204 in a range from 25% to 800%.

When thin-film mesh 100a of FIG. 2A is expanded to thin-film mesh 100b, slits 102 of thin-film mesh 100a open up into pores/fenestrations 112 to form a "chain-link" fence pattern, such as diamond-shaped pores/fenestrations. Thin-film mesh 100b forms struts 116 around each diamond-shaped pore/fenestration 112. It will be appreciated that other pore/fenestration shapes may be used in alternative embodiments. The diamond shape of each pore 112 may be longer along axis 206, also referred to as long diagonal axis 206 of diamond-shaped pore 112, and shorter along axis 204, also referred to as the short diagonal axis 204 of diamond-shaped pore 112.

FIG. 2C is a diagrammatic perspective view of thin-film mesh 100b formed by expanding thin-film mesh 100a of FIG. 2A. As shown in FIG. 2C, thin-film mesh 100b has a three-dimensional cylindrical shape. Cylindrical thin-film mesh 100b may be used, for example, as a thin-film mesh covering at least a part of an intrasaccular flow diverter, as shown in FIG. 3. Other three-dimensional shapes may be formed in other embodiments.

The pore density and the percent metal coverage may be modulated based on the type of medical treatment, the body region being treated, and/or the type of aneurysm being treated. Thin-film mesh 100a may be fabricated with slit length 114 of between 50 µm and 500 µm and expanded to thin-film mesh 100b having a pore density (fenestrations per square mm) of between 15 pores/mm² and 2217 pores/mm² and a percent metal coverage of between 6% and 83%, as described in further detail below in relation to FIGS. 11A and 11B and FIGS. 12A and 12B. Thin-film mesh 100a fabricated with slit length 114 of between 50 µm and 200 µm and expanded to thin-film mesh 100b having a high pore density of between 81 pores/mm² and 1075 pores/mm² and a low metal coverage of between 19% and 66% advantageously facilitates reconstruction of tissue defects that are superior to other pore densities and percent metal coverage, such as by promoting a planar deposition of fibrin followed by rapid cell growth (e.g., endothelialization) when placed in a blood vessel.

The orientation of slits 102 in FIG. 2A also provides advantages to thin-film mesh 100 when used as a cover for a thin-film covered medical devices. Prior to expansion, thin-film mesh 100a includes slits 102 oriented perpendicular or substantially perpendicular (e.g., oriented at an angle between 90 degrees and 60 degrees) to long axis 204 of thin-film mesh 100. After expansion along axis of expansion 204, thin-film mesh 100b includes diamond-shaped pores 112 oriented such that long diagonal axis 206 of diamond-shaped pores 112 are perpendicular to, or substantially perpendicular to, long axis 204 of thin-film mesh 100b. Accordingly, thin-film mesh 100 advantageously provides vastly improved longitudinal flexibility and expandability of the covered medical device. Further, a thin-film covered medical device that includes thin-film mesh 100 advantageously provides vastly improved flexibility to bend, arc, and/or loop around curves.

FIGS. 3A and 3B illustrate a process of forming an intrasaccular flow diverter 300. At block 302, one or more cylindrical thin-film meshes such as thin-film meshes 100 of FIGS. 1A, 1B, and 1C or FIGS. 2A, 2B, and 2C (e.g., thin-film mesh constructs formed as shown in FIGS. 9A and 9B) are placed over a length of a wire structure 312. For example, thin-film meshes 100a prior to expansion, as shown in FIG. 1A, may be placed over wire structure 312.

Thin-film meshes 100 may have slits 102 (before expansion) and pores 112 (after expansion) oriented as shown in FIGS. 1A, 1B, and 1C, such that slit axis 104 (before expansion) and long axis 104 of pores 112 (after expansion) of thin-film meshes 100 are parallel to a longitudinal axis 322 of wire structure 312.

In various embodiments, wire structure 312 is a braided wire/rope as shown in FIG. 3A. Wire structure 312 includes a plurality of individual wires (e.g., between 10 and 100 individual wires). The number of individual wires may be approximately 6, 12, 18, 24, 30, 36, 42, 48, 54, or 60 wires, where any value may form an upper end point or a lower end point, as appropriate. Wire structure 312 includes, for example, a Nitinol wire, a cobalt chromium wire, and/or other metal or metal alloy wire (e.g., a shape memory metal or metal alloy wire). Wire structure 312 may be a low density braided wire. Wire structure 312 is configured to expand laterally/radially when compressed longitudinally along axis 322 (as shown at block 306 in FIG. 3B). Wire structure 312 may be between 5 µm and 50 µm in diameter. At least one of the wires of wire structure 312 may be a radiopaque wire, which may include platinum or other radiopaque material.

Figure 15:
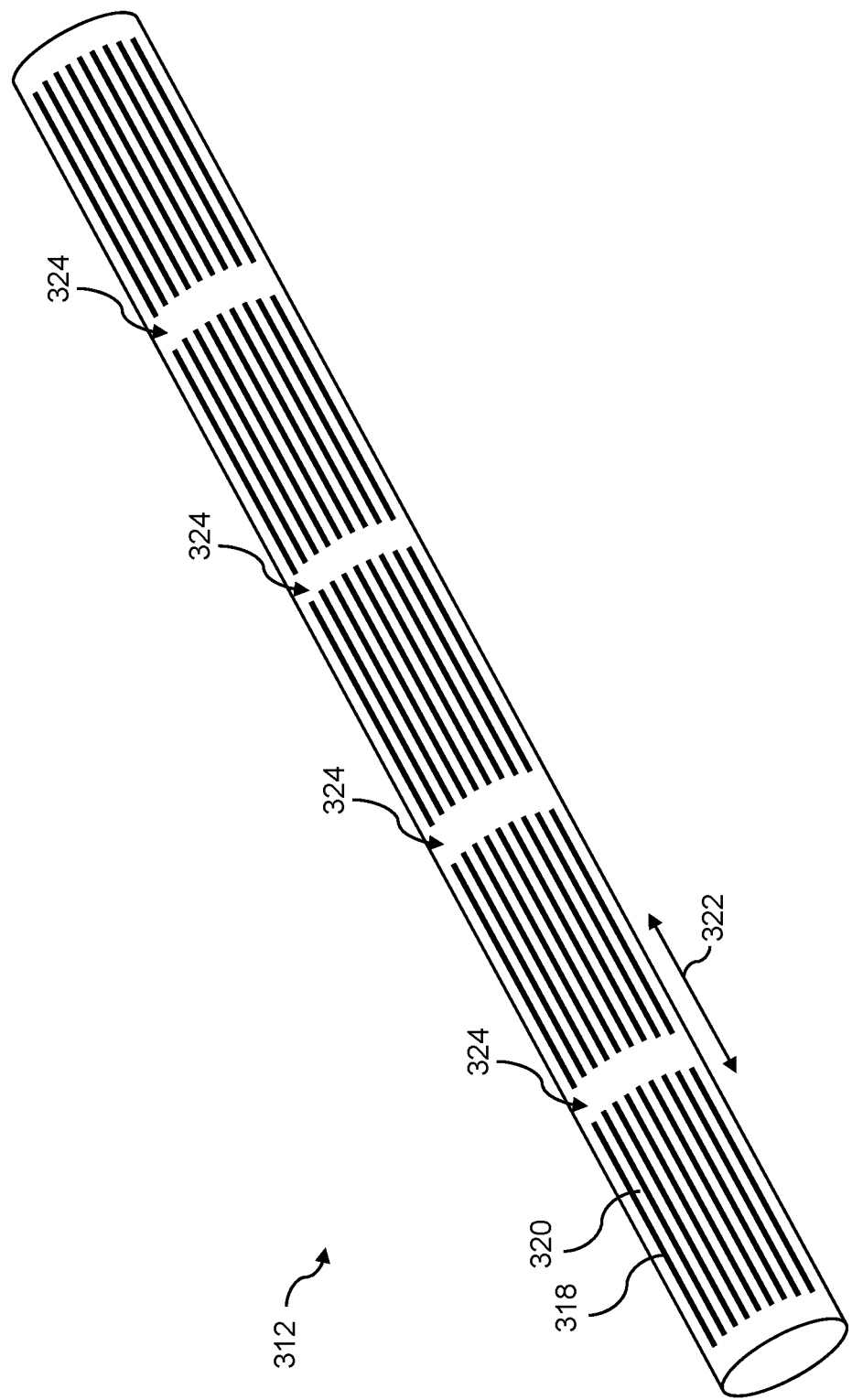
FIG. 15 is a diagrammatic perspective view of a hypotube structure for an intrasaccular flow diverter with spheroids according to an embodiment of the present disclosure.

In other embodiments, wire structure 312 is a hypotube structure as shown in FIG. 15. Hypotube structure 312 may be a laser-cut hypotube such as a laser-cut Nitinol hypotube and/or other metal or metal alloy hypotube (e.g., a shape memory metal or metal alloy hypotube). Hypotube structure 312 includes slits 318, which may be laser cut, between crimping locations 324 to form a plurality of wires 320 between crimping locations 324. For example, slits 318 include a series of slits parallel to longitudinal axis 322 of hypotube structure 312 between crimping locations 324 as shown in FIG. 15. In other examples, slits 318 include a series of slits that form an angle (e.g., greater than 0 degrees and less than 90 degrees, such as between 0 degrees and 60 degrees) with longitudinal axis 322 to form helix-shaped slits on hypotube structure 312 between crimping locations 324. The width of slits 312 (measured perpendicular to longitudinal axis 322), $W_{slit}$, and the width of wires 320 (also measured perpendicular to longitudinal axis 322), $W_{wire}$, may be related according to formula:

$$W_{slit} = \frac{C_{hypotube} - n_{wire} \times W_{wire}}{n_{slit}}$$

In the above formula, $C_{hypotube}$ is the circumference of the hypotube, $n_{slit}$ is the number of slits, and $n_{wire}$ is the number of wires. The number of slits 318, $n_{slit}$, is equal to the number of wires 320, $n_{wire}$. In an example, the width of wires 320 may be approximately equal to the wall thickness of the hypotube (e.g., between 0.05 mm to 0.5 mm). Crimping locations 324 may correspond to locations for crimps 314 provided at block 304 as described below.

At block 304, parts of thin-film meshes 100 at both ends of wire structure 312 and at one or more intermediate locations of wire structure 312 are crimped to form intrasaccular flow diverter 300a. In some embodiments, crimps 314 are provided at locations (e.g., regions or areas) in which two thin-film meshes 100 meet or one thin-film mesh 100 ends (e.g., at one or both ends of wire structure 312 and/or adjacent to a structure such as an umbrella structure at an end of wire structure 312). Crimps 314 secure thin-film mesh 100 to wire structure 312 (e.g., by attaching, engaging, fixing, holding, fastening, bonding, clamping, holding down, or otherwise coupling thin-film mesh 100 to wire structure 312). Crimps 314 may include metallic material or pseudometallic material. Radiopaque markers may be used to form at least one of crimps 314.

At block 306, intrasaccular flow diverter 300a is compressed inward, using crimps 314 as fixtures, to form expanded intrasaccular flow diverter 300b. Parts of wire structure 312 between two crimps 314 become spherical and thin-film meshes 100 are expanded. For example, parts of thin-film meshes 100a may be expanded to thin-film meshes 100b as shown in FIGS. 1A, 1B, and 1C while the crimped parts of thin-film meshes 100 remain unexpanded. Intrasaccular flow diverter 300b may thus include a plurality of microspheroids 316 (e.g., microellipsoids or microspheres) that include a part of wire structure 312 and thin-film mesh 100 that are each expanded. The shape of intrasaccular flow diverter 300b (including wire structure 312 and thin-film mesh 100 shaped as microspheroids 316) may be set in this configuration or further shaped as described below in relation to FIGS. 4A, 4B, and 4C.

Figure 4C:
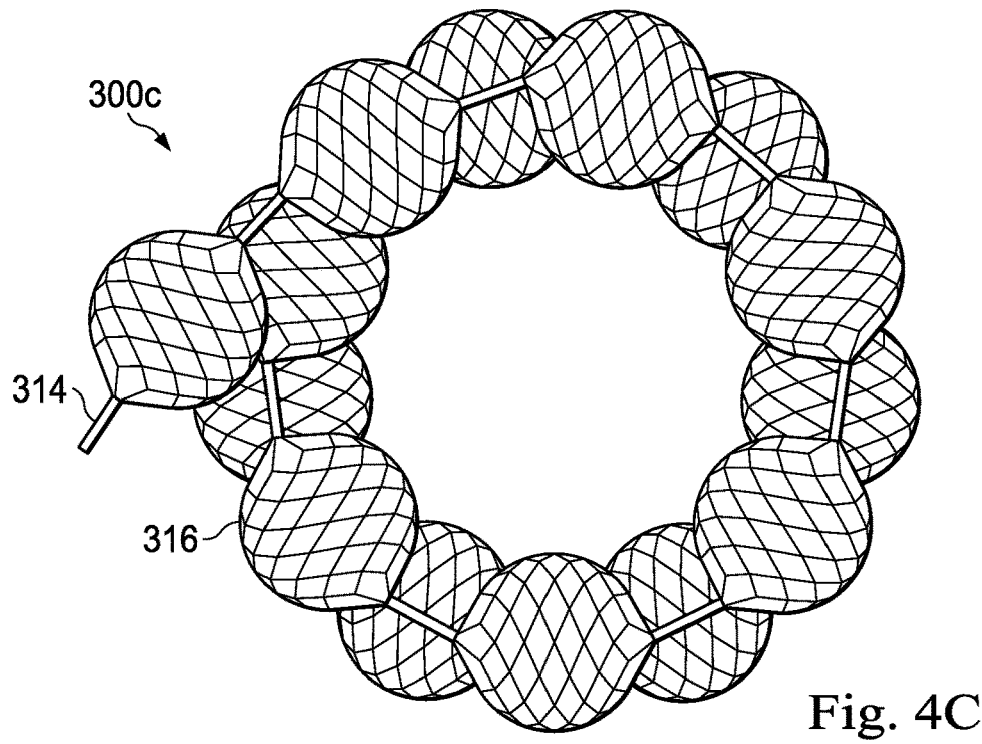

FIGS. 4A, 4B, and 4C illustrate a process of setting a shape of an intrasaccular flow diverter such as intrasaccular flow diverter 300 of FIG. 3B. FIG. 4A shows intrasaccular flow diverter 300b shaped by block 306 in FIG. 3B. Intrasaccular flow diverter 300b may further be shaped into an intrasaccular flow diverter 300c having a helical configuration. FIG. 4B shows a side elevational view of intrasaccular flow diverter 300c and FIG. 4C shows a top plan view of intrasaccular flow diverter 300c. Intrasaccular flow diverter 300b may be shaped into other three-dimensional shapes, such as a spherical shape, in other embodiments.

Figure 5A:
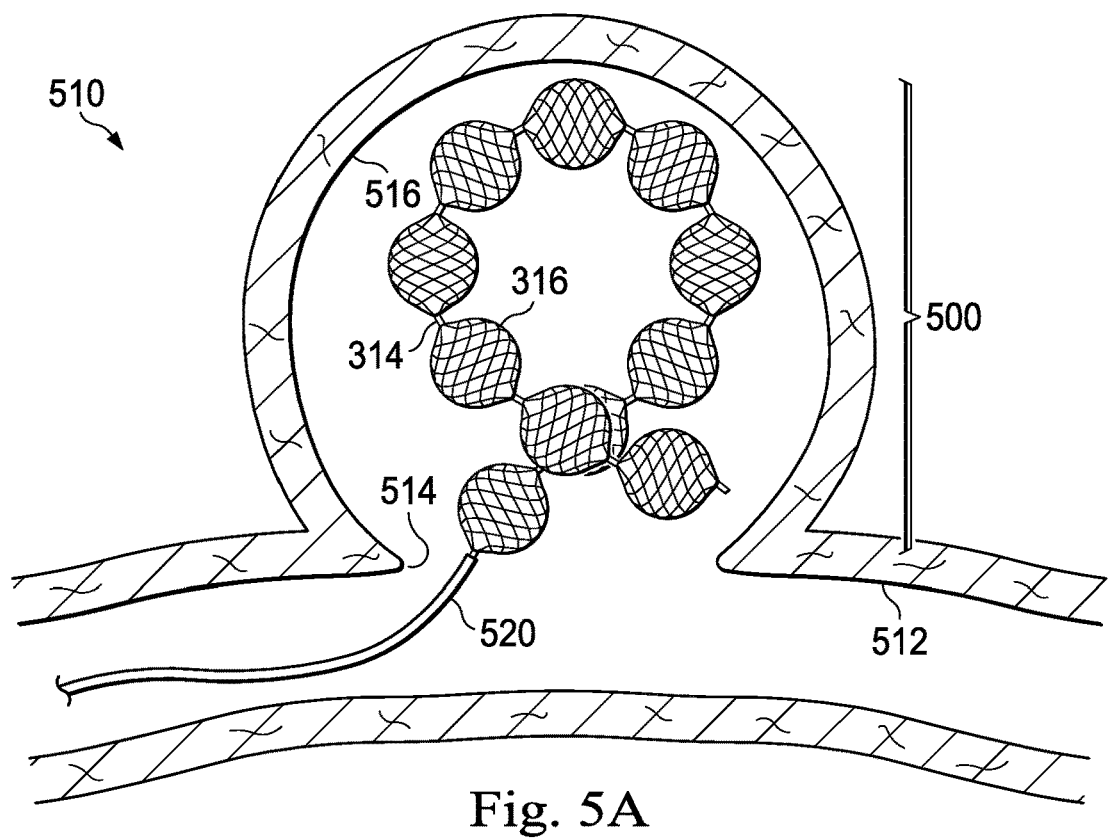
FIGS. 5A and 5B illustrate a process of deploying an intrasaccular flow diverter according to an embodiment of the present disclosure.
Figure 5B:
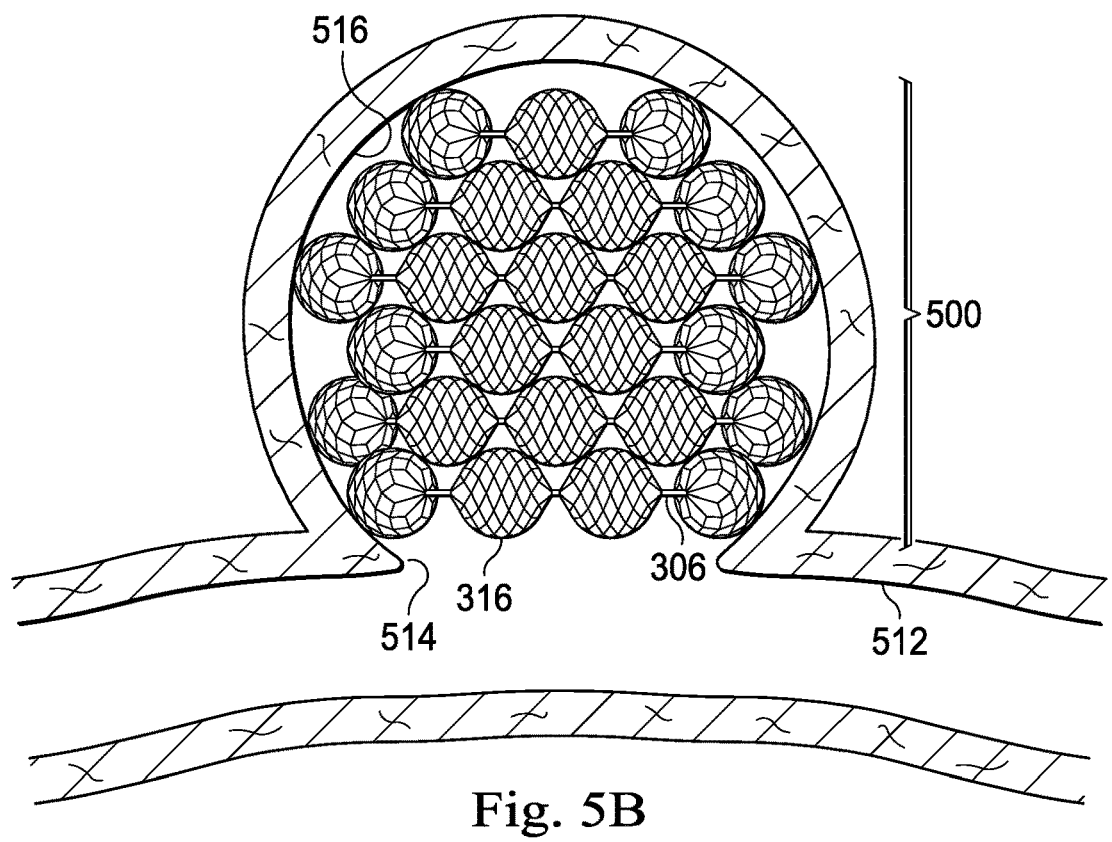

FIGS. 5A and 5B illustrate a process of deploying an intrasaccular flow diverter 500, such as intrasaccular flow diverter 300 of FIGS. 3A and 3B and FIGS. 4A, 4B, and 4C. FIG. 5A shows a cross-sectional view of an aneurysm 510 at a blood vessel 512 in which intrasaccular flow diverter 500 is being deployed using a catheter 520. Intrasaccular flow diverter 500 in its unexpanded state is placed in a catheter 520. Catheter 520 travels through blood vessels to reach blood vessel 512 and is positioned at or adjacent to a neck region 514 of aneurysm 510. Catheter then deploys intrasaccular flow diverter 500 in an aneurysm sac 516 of aneurysm 510.

FIG. 5B shows a cross-sectional view of aneurysm 510 after intrasaccular flow diverter 500 is deployed. Intrasaccular flow diverter 500 after deployment and in its expanded state includes a plurality of microspheroids 316 that fills or partially fills aneurysm sac 516. For example, intrasaccular flow diverter 500 may conform to the shape set as described in relation to FIGS. 3A and 3B and FIGS. 4A, 4B, and 4C.

Figure 6A:
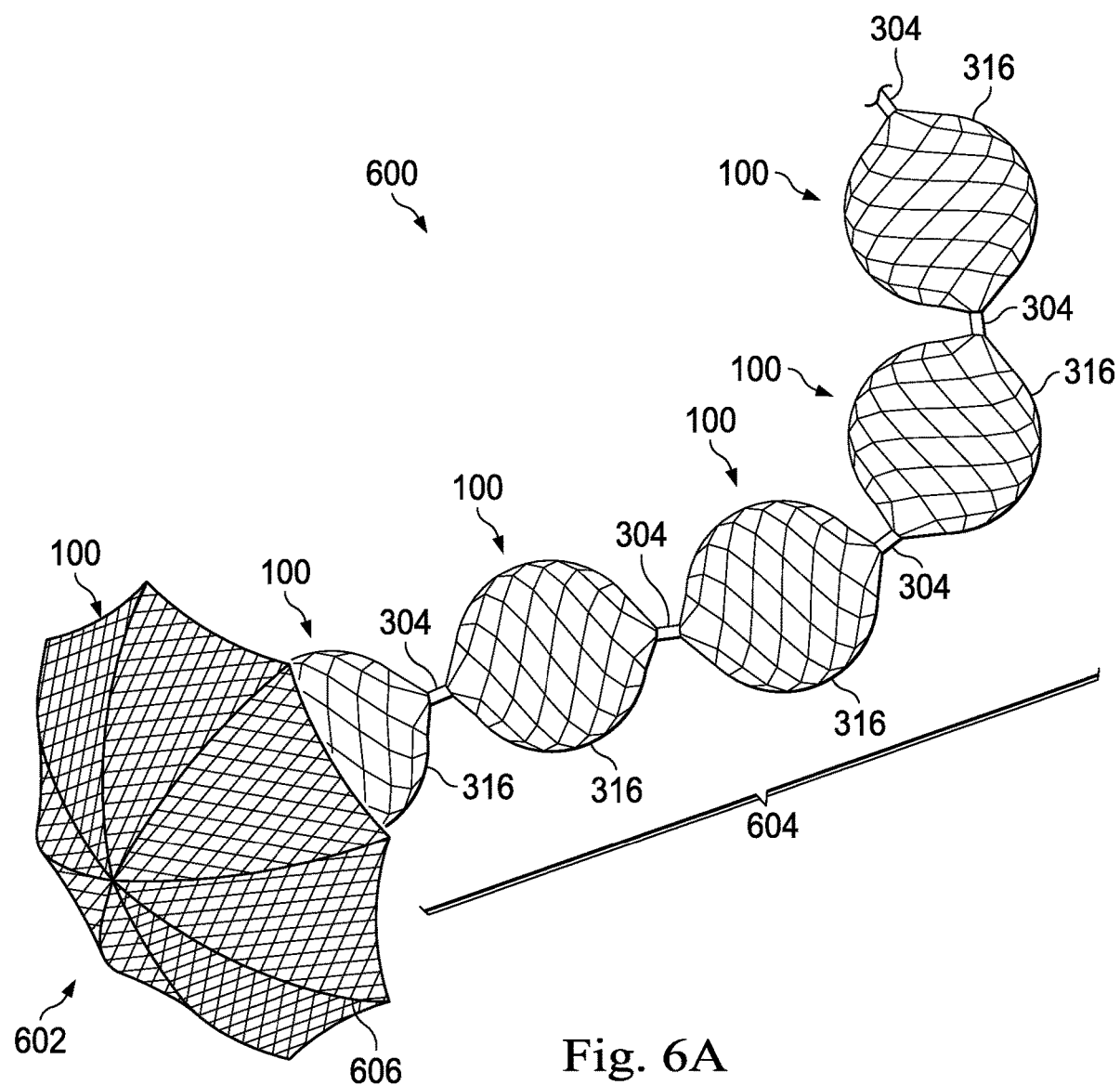
FIG. 6A is a diagrammatic perspective view of an intrasaccular flow diverter with spheroids and an umbrella structure according to an embodiment of the present disclosure.

FIG. 6A is a diagrammatic perspective view of an intrasaccular flow diverter 600 with an umbrella structure 602. Intrasaccular flow diverter 600 includes umbrella structure 602 and a device body 604. Device body 604 has a shape set to form a series of spheroids or microspheroids 316 and crimps 304 between each of microspheroids 316. Device body 604 includes wire structure 312 (as shown in FIG. 3A, not shown in FIG. 6A) covered with thin-film meshes 100 such that each of microspheroids 316 includes an expanded part of wire structure 312 covered with thin-film mesh 100. In alternative embodiments, microspheroids 316 are not covered with thin-film mesh 100.

Umbrella structure 602 is at one end of intrasaccular flow diverter 600. Umbrella structure 602 is covered with thin-film mesh 100 (e.g., a thin-film mesh having a high pore density between 50 and 500 pores/mm$^2$). Umbrella structure 602 may include struts 606 (e.g., wire struts) and thin-film mesh 100 placed over and secured to struts 606 to provide thin-film mesh 100 between struts 606 (e.g., by attaching, engaging, fixing, holding, fastening, bonding, clamping, holding down, or otherwise coupling thin-film mesh 100 to struts 606 and/or wire structure 312). Alternatively, umbrella structure 602 is covered with a thin-film sheet that does not have micropatterned pores (e.g., a solid, non-porous thin-film sheet, such as a non-porous TFN sheet). As umbrella structure 602 is deployed inside an aneurysm, there may be no risk or less risk of blocking a perforator or a healthy branch vessel by using a non-porous thin-film sheet to cover umbrella structure 602.

The other end of intrasaccular flow diverter 600 may include crimp 304 of microsphere 316. In other embodiments, the other end of intrasaccular flow diverter 600 also includes an umbrella structure such as umbrella structure 602. The umbrella structure at the other end may include no thin-film mesh or non-porous thin-film sheet as this umbrella structure will not cover a neck of an aneurysm when deployed (e.g., this umbrella structure may face an interior wall of an aneurysm sac). Alternatively, the umbrella structure at the other end may also be covered with thin-film mesh 100 or a non-porous thin-film sheet.

In other embodiments, only umbrella structure 602 is covered with thin-film mesh 100, and microspheroids 316 are not covered with thin-film mesh 100. In further embodiments, umbrella structure 602 and one or more microspheroids 316 (e.g., microspheroids 316 closer to umbrella structure 602) are covered with thin-film mesh 100 while other microspheroids 316 (e.g., microspheroids 316 closer to the other end) are not covered with thin-film mesh 100.

In some embodiments, umbrella structure 602 is formed from an end of wire structure 312 such that umbrella structure 602 extends from wire structure 312 (e.g., a braided wire or laser-cut hypotube). In other embodiments, umbrella structure 602 is a separate structure attached to an end of wire structure 312. Umbrella structure 602 may be formed from a plurality of wires (e.g., a Nitinol wire, a cobalt chromium wire, and/or other metal or metal alloy wire) or a laser-cut hypotube (e.g., a Nitinol hypotube and/or other metal or metal alloy hypotube).

Figure 6B:
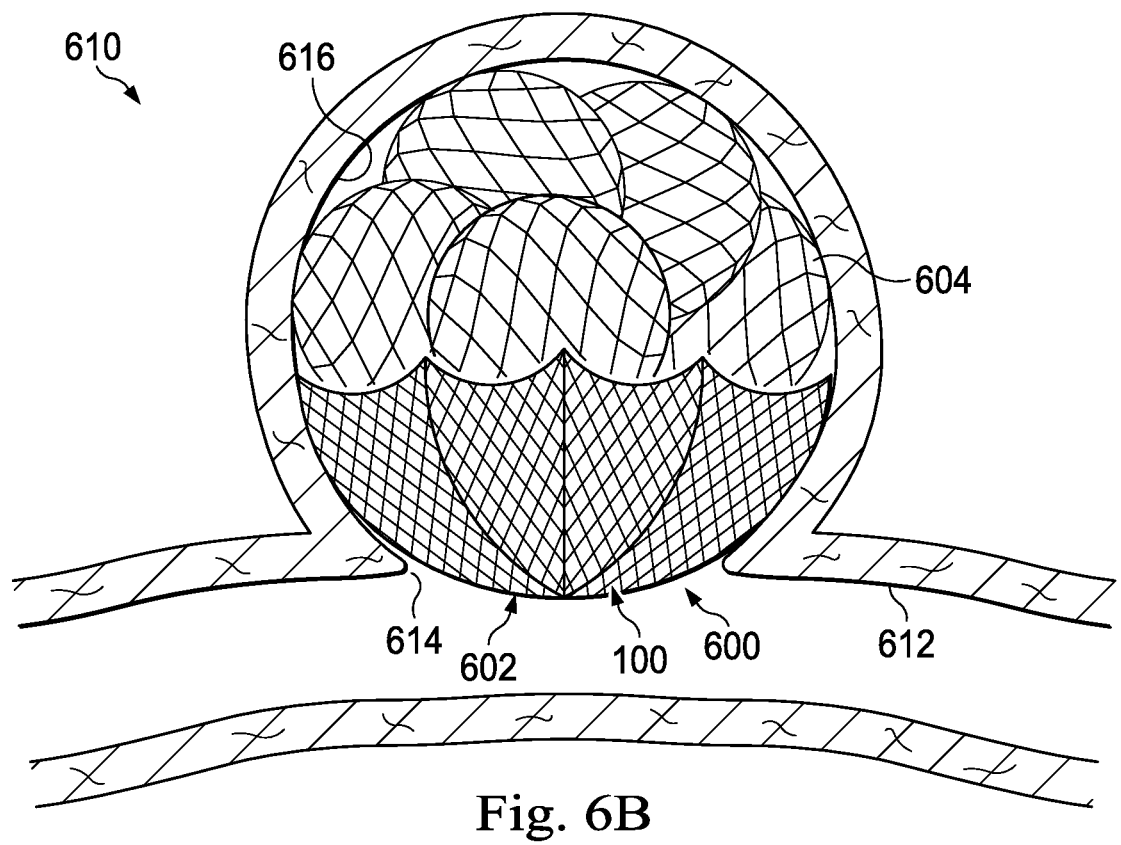
FIG. 6B is a diagrammatic cross-sectional view of an aneurysm in which the intrasaccular flow diverter of FIG. 6A is implanted.

FIG. 6B is a diagrammatic cross-sectional view of an aneurysm 610 in which the intrasaccular flow diverter 600 of FIG. 6A is implanted. A catheter may be used to move intrasaccular flow diverter 600 to blood vessel 612 and deliver intrasaccular flow diverter 600 through aneurysm neck 614 into aneurysm sac 616, as described above in relation to FIGS. 5A and 5B. Umbrella structure 602 with thin-film mesh 100 covers aneurysm neck 614, and thin-film mesh 100 covering umbrella structure 602 facilitates regrowth of vessel wall. Microspheroids 316 of intrasaccular flow diverter 600 fills or partially fills aneurysm sac 616. Advantageously, microspheroids 316 of device body 604 volumetrically fills aneurysm sac 616 to limit intrasaccular blood flow, and thin-film meshes 100 of microspheroids 316 provide a scaffold for tissue ingrowth and blood clotting reaction. Further, device body 604 and umbrella structure 602 may exert pressure on aneurysm walls, which keeps umbrella structure 602 in place at aneurysm neck 614.

Figure 7:
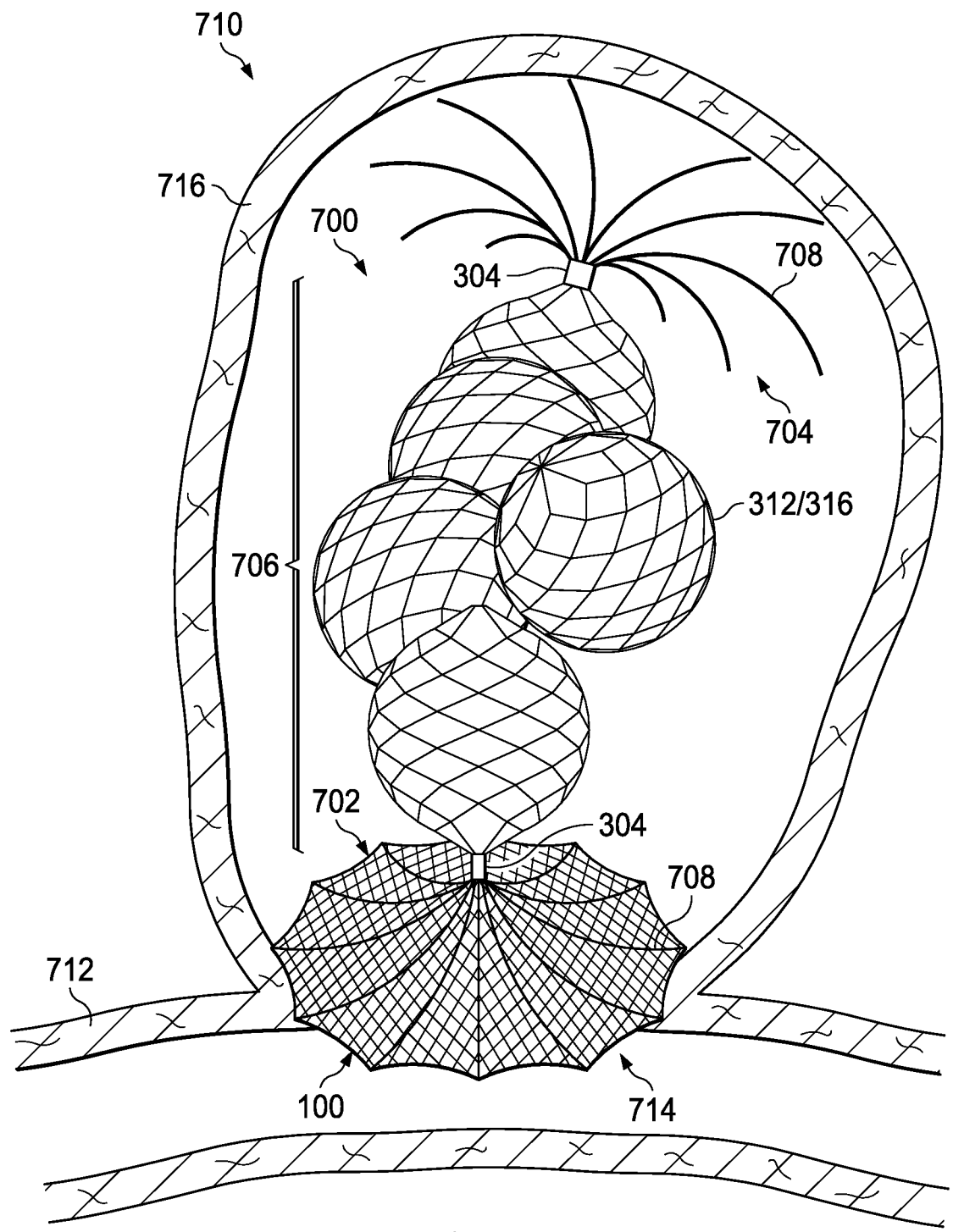
FIG. 7 is a diagrammatic cross-sectional view of an aneurysm in which an intrasaccular flow diverter with spheroids and an umbrella structure at each end according to an embodiment of the present disclosure.

FIG. 7 is a diagrammatic cross-sectional view of an aneurysm 710 in which an intrasaccular flow diverter 700 with umbrella structures 702, 704 is implanted. Intrasaccular flow diverter 700 includes an umbrella structure 702 (e.g., a proximal umbrella), umbrella structure 704 (e.g., a distal umbrella) and a device body 706 between umbrella structure 702 and umbrella structure 704. Device body 706 has a shape set to form a series of microspheroids 316 and crimps 304 between each of microspheroids 316.

Umbrella structure 702 at one end (e.g., the proximal end) of intrasaccular flow diverter 700 is covered with thin-film mesh 100 (e.g., a thin-film mesh having a high pore density between 50 and 500 pores/mm$^2$). Umbrella structure 702 may include struts 708 and thin-film mesh 100 placed over and secured to struts 708 to provide thin-film mesh 100 between struts 708 (e.g., by attaching, engaging, fixing, holding, fastening, bonding, clamping, holding down, or otherwise coupling thin-film mesh 100 to struts 708 and/or wire structure 312). Thin-film mesh 100 of umbrella structure 702 facilitates tissue in-growth at aneurysm neck 714 and limits intrasaccular blood flow. Alternatively, umbrella structure 702 is covered with a with a thin-film sheet that does not have micropatterned pores (e.g., a solid, non-porous thin-film sheet, such as a non-porous TFN sheet). As umbrella structure 702 is deployed inside aneurysm 710, there may be no risk or less risk of blocking a perforator or a healthy branch vessel by using a non-porous thin-film sheet to cover umbrella structure 702.

Umbrella structure 704 at the other end (e.g., the distal end) of intrasaccular flow diverter is not covered with thin-film mesh 100 or a non-porous thin-film sheet. Intrasaccular flow diverter 700 includes struts 708 without thin-film mesh 100 or a thin-film sheet placed over and attached to struts 708. In an alternative embodiment, umbrella structure 704 is also covered with thin-film mesh 100. Umbrella structure 704 exerts a force against the wall of aneurysm sac 716 to appose umbrella structure 702 against aneurysm neck 714.

Device body 706 includes wire structure 312, with a plurality of parts of wire structure 312 shape set to microspheroids 316 such that device body 706 forms microspheroids in its expanded state. Microspheroids 316 of intrasaccular flow diverter 700 fills or partially fills aneurysm sac 716. Advantageously, microspheroids 316 of device body 706 volumetrically fills aneurysm sac 716 to limit intrasaccular blood flow. Microspheroids 316 may be springy, being configured to compress and expand to help appose umbrella structure 702 against aneurysm neck 714. In the embodiment shown in FIG. 7, microspheroids 316 are not covered with thin-film mesh 100, but in alternative embodiments microspheroids 316 may be covered with thin-film mesh 100 as intrasaccular flow diverter 300 of FIG. 3B and FIGS. 4A, 4B, and 4C, intrasaccular flow diverter 500 of FIGS. 5A and 5B, and intrasaccular flow diverter 600 of FIGS. 6A and 6B.

In some embodiments, umbrella structures 702, 704 are formed from respective ends of wire structure 312 such that umbrella structures 702, 704 are extensions of wire structure 312 (e.g., a braided wire or laser-cut hypotube). In other embodiments, umbrella structures 702, 704 are separate structures attached to respective ends of wire structure 312. Umbrella structures 702, 704 may each be formed from a plurality of wires (e.g., a Nitinol wire, a cobalt chromium wire, and/or other metal or metal alloy wire) or a laser-cut hypotube (e.g., a Nitinol wire, a cobalt chromium wire, and/or other metal or metal alloy wire).

Figure 8:
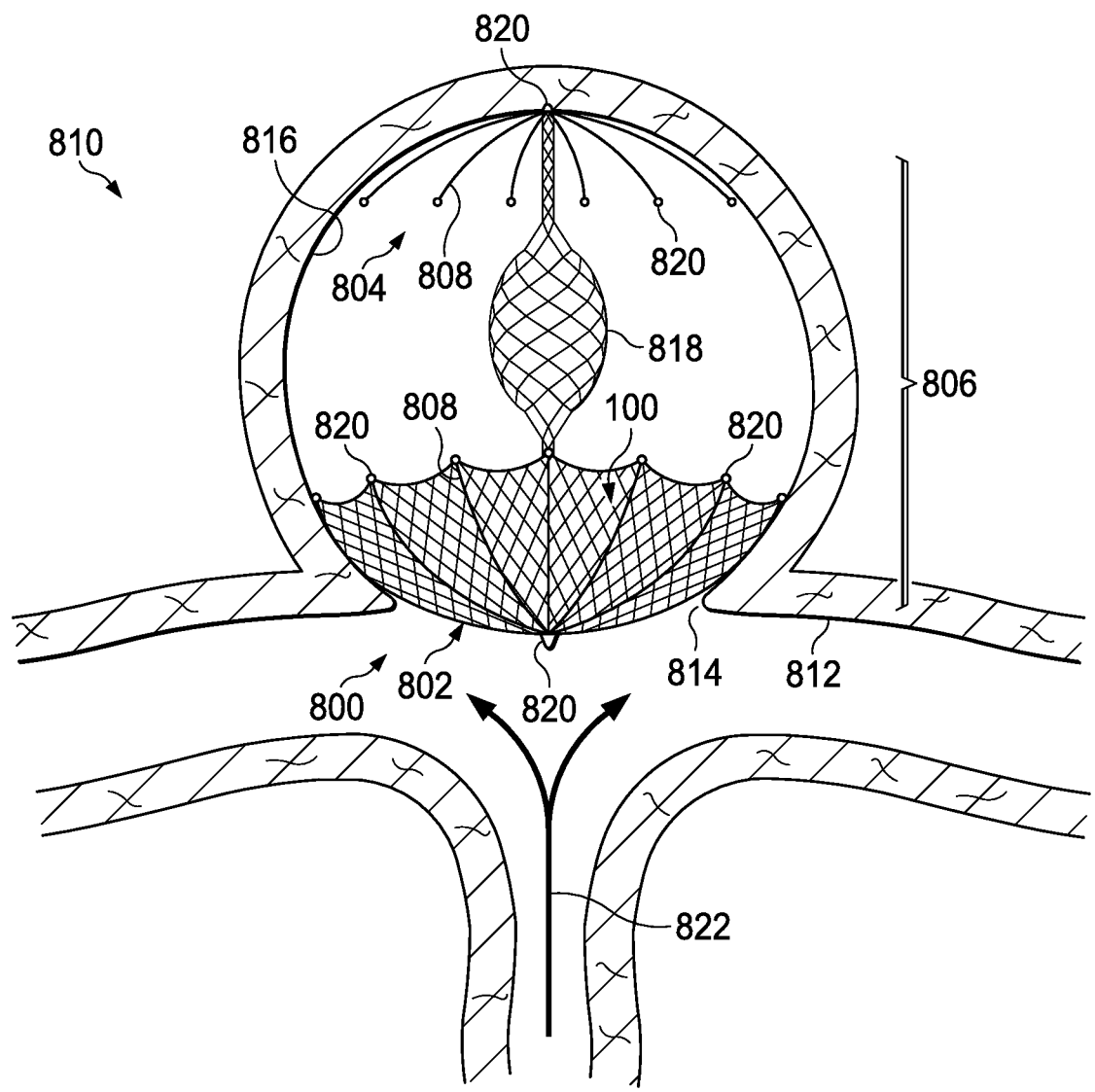
FIG. 8 is a diagrammatic cross-sectional view of an aneurysm in which an intrasaccular flow diverter with a central spring and an umbrella structure at each end according to an embodiment of the present disclosure.

FIG. 8 is a diagrammatic cross-sectional view of an aneurysm 810 in which an intrasaccular flow diverter 800 with umbrella structures 802, 804 is implanted. Intrasaccular flow diverter 800 includes an umbrella structure 802 (e.g., a proximal umbrella), umbrella structure 804 (e.g., a distal umbrella) and a device body 806 between umbrella structure 802 and umbrella structure 804. Device body 806 has a shape set to form a single spheroid spring 818 (e.g., a spherical spring or an oval spring). Spheroid spring 818 is provided between umbrella structure 804 and umbrella 802. For example, spheroid spring 818 may be a central spheroid spring provided at the center or approximately at the center between umbrella structure 804 and umbrella structure 802. Alternatively, spheroid spring 818 may be closer to one of umbrella structures 802, 804 than the other. Although aneurysm 810 shown in FIG. 8 is a bifurcation aneurysm, intrasaccular flow diverter 800 may be used for other aneurysms such as sidewall aneurysms. Intrasaccular flow diverter 800 facilitates blood flow 822 to flow along blood vessels 812 by limiting blood flow 822 from entering aneurysm 810 and diverting blood flow 822 along blood vessels 812.

Umbrella structure 802 at one end (e.g., the proximal end) of intrasaccular flow diverter 800 is covered with thin-film mesh 100 (e.g., a thin-film mesh having a high pore density between 50 and 500 pores/mm$^2$). Umbrella structure 802 may include umbrella struts 808 and thin-film mesh 100 placed over and secured to struts 808 to provide thin-film mesh 100 between struts 808 (e.g., by attaching, engaging, fixing, holding, fastening, bonding, clamping, holding down, or otherwise coupling thin-film mesh 100 to struts 808 and/or wire structure 312). Thin-film mesh 100 of umbrella structure 802 facilitates tissue in-growth at aneurysm neck 814 and limits intrasaccular blood flow. Alternatively, umbrella structure 802 is covered with a thin-film sheet that does not have micropatterned pores (e.g., a solid, non-porous thin-film sheet, such as a non-porous TFN sheet). As umbrella structure 802 is deployed inside aneurysm 810, there may be no risk or less risk of blocking a perforator or a healthy branch vessel by using a non-porous thin-film sheet to cover umbrella structure 802.

Umbrella structure 804 at the other end (e.g., the distal end) of intrasaccular flow diverter is not covered with thin-film mesh 100 or a non-porous thin-film sheet. Intrasaccular flow diverter 800 includes struts 808 without thin-film mesh 100 or a thin-film sheet placed over and attached to struts 808. In an alternative embodiment, umbrella structure 804 is also covered with thin-film mesh 100.

Device body 806 includes wire structure 312 (as shown in FIG. 3A, not shown in FIG. 8) covered with thin-film meshes 100 that are shape-set to form spheroid spring 818 such that spheroid spring 818 provides a longitudinal spring force to push umbrella structure 804 and umbrella structure 802 outwardly when compressed. Spheroid spring 818 modulates the height of intrasaccular flow diverter 800 to accommodate varying anatomy of aneurysm 810.

When deployed in aneurysm 810, spheroid spring 818 is at least partially compressed and pushes umbrella structures 802, 804 outwardly. Umbrella structure 804 exerts a force against the wall of aneurysm sac 816 to appose umbrella structure 802 against aneurysm neck 814. Umbrella structure 802 exerts a force towards aneurysm neck 814 and struts 808 of umbrella structure 802 spread such force to wall areas adjacent to aneurysm neck 814. Advantageously, intrasaccular flow diverter 800 is able to conform to a wide range of anatomy and achieve aneurysm occlusion with placement of a single device.

In some embodiments, umbrella structures 802, 804 are formed from respective ends of wire structure 312 such that umbrella structures 802, 804 are extensions of wire structure 312 (e.g., a braided wire or laser-cut hypotube). In other embodiments, umbrella structures 802, 804 are separate structures attached to respective ends of wire structure 312. Umbrella structures 802, 804 may each be formed from a plurality of wires (e.g., a Nitinol wire, a cobalt chromium wire, and/or other metal or metal alloy wire) or a laser-cut hypotube (e.g., a Nitinol wire, a cobalt chromium wire, and/or other metal or metal alloy wire).

In one embodiment, device body 806 and umbrella structures 802, 804 are formed from a single braided wire 312 as shown in FIG. 16A. One end of braided wire 312 extending from crimp 314a expands radially to form struts 808 for umbrella structure 802. The other end of braided wire 312 extending from crimp 314b expands radially to form struts 808 for umbrella structure 804. The middle of braided wire 312 between two crimps 314c expands radially to form spheroid spring 818. Braided wire 312 may be shape-set after radial expansion to provide backbone structure of intrasaccular flow diverter 800 shown in FIG. 8. Accordingly, the middle portion of braided wire 312 corresponds to device body 806, which is flanked by one end of braided wire 312 corresponding to umbrella structure 802 and the other end of braided wire 312 corresponding to umbrella structure 804. Portions of braided wire 312 corresponding to device body 806, umbrella structure 802, and/or umbrella structure 804 may be covered with thin-film mesh 100 before or after expansion/shape setting.

In another embodiment, device body 806 and umbrella structures 802, 804 are formed from a single hypotube structure 312 as shown in FIG. 16B. Slits 318 at one end of hypotube structure 312 form a set of wires 320 that expand radially to form struts 808 of umbrella structure 802. Slits 318 at the other end of hypotube structure 312 form a set of wires 320 that expand radially to form struts 808 of umbrella structure 804. Slits 318 in the middle of hypotube structure 312 form a set of wires 320 (which may be covered with mesh 100) that expand radially to form spheroid spring 818. In an example, slits 318 may include a series of slits parallel to longitudinal axis 322 of hypotube structure 312 as shown in FIG. 16B. In other examples, slits 318 may include a series of slits that form an angle (e.g., greater than 0 degrees and less than 90 degrees, such as between 0 degrees and 60 degrees) with longitudinal axis 322 to form helix-shaped slits on hypotube structure 312. The width of slits 312 (measured perpendicular to longitudinal axis 322), $W_{slit}$, and the width of wires 320 (also measured perpendicular to longitudinal axis 322), $W_{wire}$, may be related according to formula:

$$W_{slit} = \frac{C_{hypotube} - n_{wire} \times W_{wire}}{n_{slit}}$$

In the above formula, $C_{hypotube}$ is the circumference of the hypotube, $n_{slit}$ is the number of slits, and $n_{wire}$ is the number of wires. The number of slits 318, $n_{slit}$, is equal to the number of wires 320, $n_{wire}$. For example, the width of wires 320 may be approximately equal to the wall thickness of the hypotube (e.g., between 0.05 mm to 0.5 mm). Hypotube structure 312 may be shape-set to provide backbone structure of intrasaccular flow diverter 800 shown in FIG. 8. Accordingly, the middle portion of hypotube structure 312 corresponds to device body 806, which is flanked by one end of hypotube structure 312 corresponding to umbrella structure 802 and the other end of hypotube structure 312 corresponding to umbrella structure 804. Portions of hypotube structure 312 corresponding to device body 806, umbrella structure 802, and/or umbrella structure 804 may be covered with thin-film mesh 100 before or after expansion/shape setting.

In a further embodiment, device body 806 is formed from a braided wire 312, and umbrella structures 802, 804 are formed from laser-cut hypotubes. Umbrella structures 802, 804 are attached to respective ends of device body 806 before or after shape-setting to provide backbone structure of intrasaccular flow diverter 800 shown in FIG. 8.

In some embodiments, an intrasaccular flow diverter such as intrasaccular flow diverter 300, 500, 600, 700, or 800 includes one or more radiopaque markers (e.g., provided on respective umbrella structures and/or crimps 304). For example, intrasaccular flow diverter 800 of FIG. 8 includes radiopaque markers 820 provided at ends of umbrella struts 808. Further, in some embodiments, intrasaccular flow diverter such as intrasaccular flow diverter 300, 500, 600, 700, or 800 includes one or more thin-film meshes 100 (e.g., a TFN mesh) that are configured to deliver small molecules, biological macromolecules, or cells to provide further therapeutic effects.

Figure 9A:
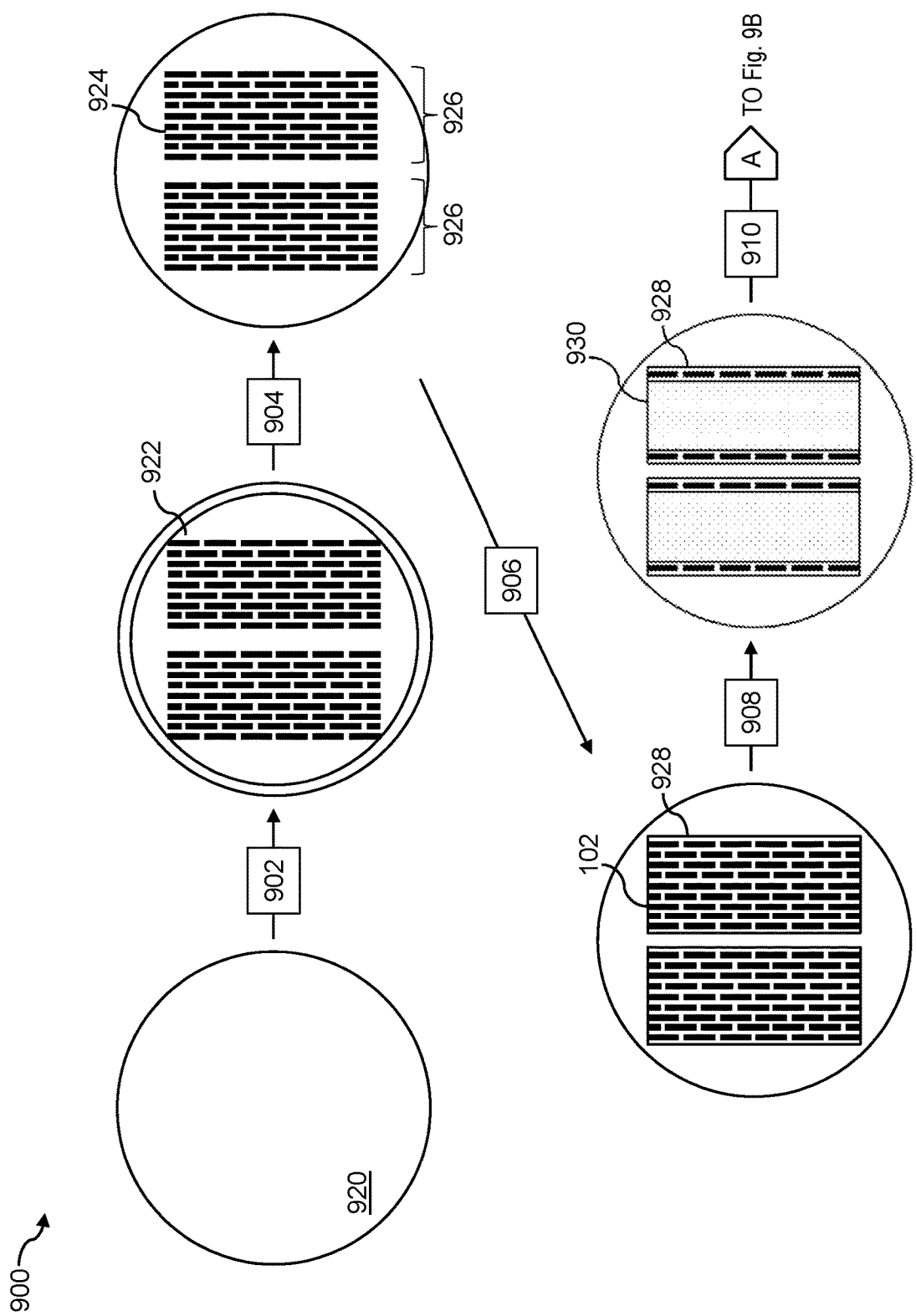

FIGS. 9A and 9B illustrate a process 800 of fabricating a thin-film mesh, such as thin-film mesh 100 of FIGS. 1A, 1B, and 1C or FIGS. 2A, 2B, and 2C, for a device that includes thin-film mesh 100, such as intrasaccular flow diverter 300 of FIG. 3B and FIGS. 4A, 4B, and 4C, intrasaccular flow diverter 500 of FIGS. 5A and 5B, intrasaccular flow diverter 600 of FIGS. 6A and 6B, intrasaccular flow diverter 700 of FIG. 7 and/or intrasaccular flow diverter 800 of FIG. 8. At block 902, a photoresist 922 is spun coated on a substrate such as silicon wafer 920 and patterned using photolithography. Patterned photoresist 922 (shown in black) leaves exposed areas of wafer 920 (shown in white) available for etching.

At block 904, deep reactive ion etching (DRIE) is used to create trenches 924 at the exposed areas of wafer 920 and photoresist 922 is removed. Trenches 924 may be, for example, between 25 µm and 200 µm deep into substrate 920. Trenches 924 may form a micropattern 926 that provide a template for thin-film mesh 100. The resolution of the micropattern using the DRIE process may be approximately 1 µm. Although two micropatterns 926 are shown, wafer 920 may include more micropatterns 926.

At block 906, a Nitinol layer 928 is formed on micropattern 926 on wafer 920. For example, a sacrificial layer or lift-off layer (e.g., a copper and/or chromium layer deposited by e-beam evaporation) and then an inhibition layer or barrier layer (e.g., SiO$_2$ layer deposited by Plasma-enhanced chemical vapor deposition (PECVD)) may be deposited. Then, a Nitinol layer 928 is sputter deposited on wafer 920. Nitinol layer 928 may have a thickness of between 1 to 20 µm. Trenches 924 of wafer 920 are duplicated on Nitinol layer 928 as corresponding fenestrations (e.g., closed fenestrations), such as slits 102 in FIG. 1A or FIG. 2A, as sputtered Nitinol at regions corresponding to trenches 924 fall to the bottom of trenches 924. The resulting patterns of fenestrations may also be denoted as a fiche in that the fenestrations are in closed form prior to an expansion of the TFN sheet. Just like a microfiche, each fiche or pattern of fenestrations effectively codes for the resulting fenestrations when the thin-film mesh is expanded to fully open up the fenestrations.

At block 908, a sacrificial layer 930 is deposited to cover a portion of Nitinol layer 928 while leaving long edges of Nitinol layer 928 exposed. A bonding metal, for example aluminum, may be deposited at the exposed long edge that will serve to anneal the two nitinol layers when the bonding metal is heated to its melting temperature. For example, a barrier layer may be deposited, followed by sacrificial layer 930, followed by another barrier layer.

At block 910, a Nitinol layer 932 is formed on top of sacrificial layer 930 and the exposed edges of Nitinol layer 928. For example, Nitinol layer 932 may be sputter deposited on top of sacrificial layer 930 and the exposed edges of Nitinol layer 928. Nitinol layer 932 may have a thickness of approximately 1 to 20 µm. Similarly to block 906, trenches 924 of wafer 920 are duplicated on Nitinol layer 932 as corresponding fenestrations (e.g., closed fenestrations), such as slits 102 in FIG. 1A or FIG. 2A, as sputtered Nitinol at regions corresponding to trenches 924 fall to the bottom of trenches 924. Nitinol layer 928 and Nitinol layer 932 may be joined at the longitudinal edges to form thin-film mesh 100a of FIG. 1A or FIG. 2A.

At block 912, thin-film mesh 100a is removed from wafer 920 using a lift-off process by etching away sacrificial layers including sacrificial layer 930. Thin-film mesh 100a is removed from the surface of wafer 920 (i.e., the top layer as opposed to the bottom layer at the bottom of trenches 924.) Barrier layers may also be removed. The resulting thin-film mesh 100a includes Nitinol layer 928 and Nitinol layer 932 joined at the longitudinal edges.

At block 914, thin-film mesh 100a may be expanded to thin-film mesh 100b of FIGS. 1B and 1C or FIGS. 2B and 2C. Expanded thin-film mesh 100b may form a three-dimensional cylindrical tube and have fenestrations 112 that have been opened up. Other three-dimensional shapes may be formed by process 900 in other embodiments.

In some embodiments, thin-film mesh 100a is attached to a braided wire and/or an umbrella structure of intrasaccular flow diverter 300, 500, 600, 700, or 800 after block 912 without expanding to thin-film mesh 100b, and is expanded at block 914 as a part of intrasaccular flow diverter 300, 500, 600, 700, or 800. In other embodiments, thin-film mesh 100a is expanded at block 914 to thin-film mesh 100b and then attached to a braided wire and/or an umbrella structure of intrasaccular flow diverter 300, 500, 600, 700, or 800.

Thin film meshes, such as thin-film mesh 100 of FIGS. 1A, 1B, and 1C or FIGS. 2A, 2B, and 2C, that may be used for an intrasaccular flow diverter such as intrasaccular flow diverter 300, 500, 600, 700, or 800 and processes for fabricating such thin-film meshes are further described in International Application No. PCT/US2016/039436, entitled "Thin-Film Micromesh Covers for Medical Devices and Related Methods," filed on Jun. 24, 2016, and International Application No. PCT/US2016/040864, entitled "Thin-Film Micromesh Medical Devices and Related Methods," filed on Jul. 1, 2016, which are hereby incorporated by reference in their entirety.

Figure 10B:
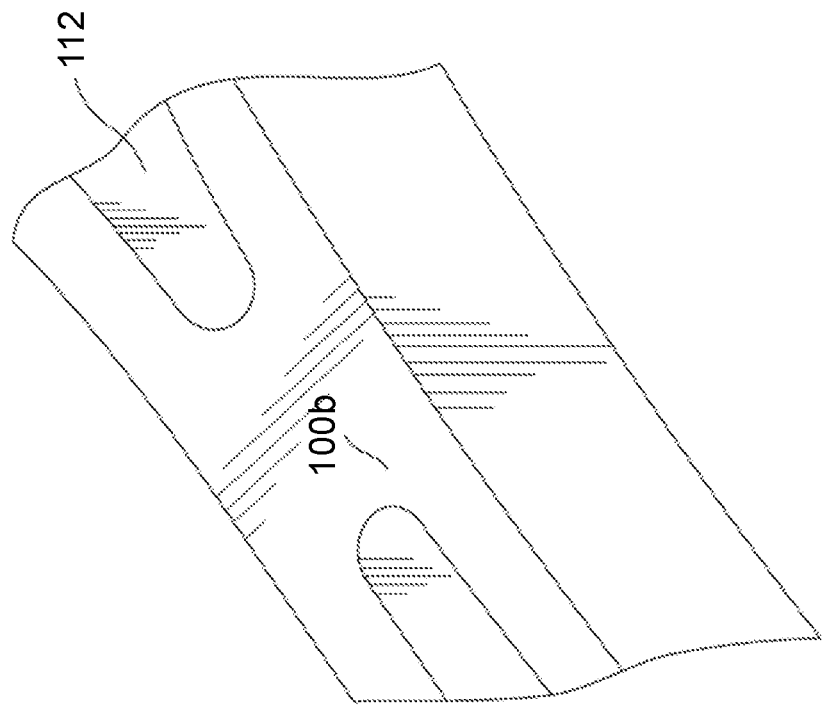
FIGS. 10A and 10B are diagrammatic close-up views of a thin-film mesh according to an embodiment of the present disclosure.
Figure 10A:
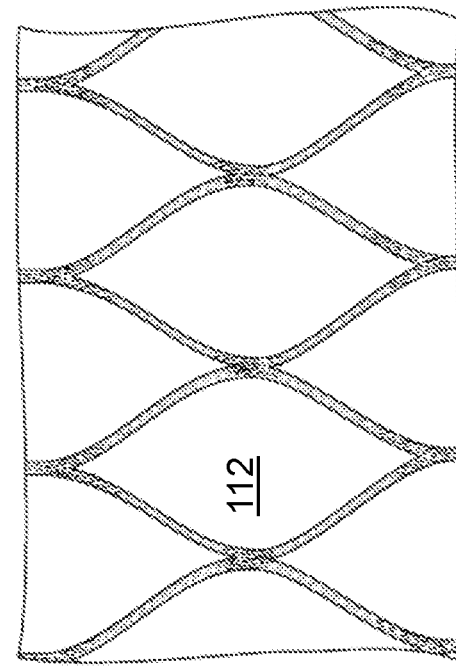

FIG. 10A is a diagrammatic close-up plan view of a portion of thin-film mesh 100b in FIGS. 1B and 1C or FIGS. 2B and 2C. Thin-film mesh 100b may have diamond-shaped pores 112 fabricated as slits 102 having slit length 114 of between 50 µm and 300 µm. Thin-film mesh 100b may have a pore density of between 70 pores/mm$^2$ and 1075 pores/mm$^2$, and a percent metal coverage of between 14% and 66%.

FIG. 10B is a diagrammatic close-up perspective view of a portion of thin-film mesh 100b in FIGS. 1B and 1C or FIGS. 2B and 2C. Conventional intrasaccular flow diverters made with wire meshes are not flat where the wires intertwine. In contrast, because thin-film mesh 100b is made with a layer of material such as Nitinol and expanded, there is no intertwining of wires. Thus, thin-film mesh is flat all around pores 112, which is advantageous for promoting rapid deposition of fibrin and cell growth (e.g., endothelialization).

Figure 11B:
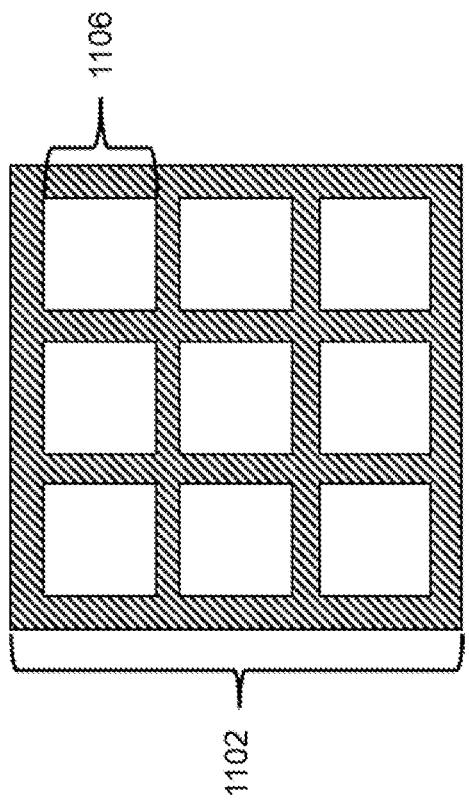
FIGS. 11A and 11B illustrate thin-film mesh fenestration designs that have the same porosity but different pore densities according to various embodiments of the present disclosure.
Figure 11A:
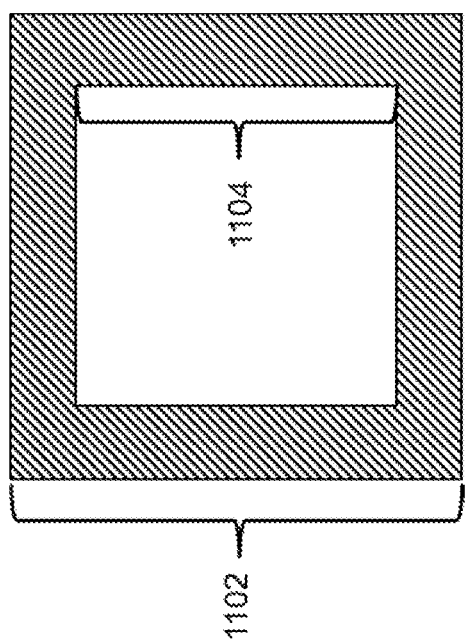

FIGS. 11A and 11B illustrate thin-film mesh fenestration designs that have the same porosity but different pore densities. The primary characteristics that determine the degree of flow diversion are percent metal coverage (PMC) and pore density, where higher percent metal coverage and higher pore density yield an increased flow diverting effect. Percent metal coverage is the fraction of the area of metal over the total area. Porosity is the fraction of the open area over the total area. Accordingly, for expanded thin-film mesh 100b, the porosity and percent metal coverage of thin-film mesh 100b add up to 1, or 100%. Similarly, for an intrasaccular thin-film flow diverter (e.g., a thin-film covered intrasaccular flow diverter), the porosity of the intrasaccular thin-film flow diverter, the percent metal coverage of thin-film mesh 100b, and the percent metal coverage of the expanded braided wire add up to 1, or 100%.

The surface shown in FIG. 11A has a length 1102 of 1 mm and a length 1104 of 0.71 mm, such that the surface has a porosity of 50%, a pore density of 1 pore/mm$^2$, and a total edge length of 2.84 mm. The surface shown in FIG. 11B has a length 1102 of 1 mm and a length 1106 of 0.24 mm, such that the surface has a porosity of 50%, a pore density of 9 pore/mm$^2$, and a total edge length of 8.64 mm. Even though the pore designs of FIG. 11A and FIG. 11B have the same porosity of 50%, the design in FIG. 11A has a pore density of 1 pore/area while the design in FIG. 11B has a pore density of 9 pores/area. For intrasaccular thin-film flow diverters, two intrasaccular thin-film flow diverters having similar porosity and percent metal coverage may have drastically different efficacy due to different pore density. For example, intrasaccular thin-film flow diverters with a percent metal coverage of 25-35% and 150-250 pores/mm$^2$ are vastly superior to conventional intrasaccular flow diverters, which may have a percent metal coverage of 35% and 14 pores/mm$^2$, because the increased pore density provides more friction per unit area and provides a surface for fibrin deposition and cell growth (e.g., endothelialization). Indeed, intrasaccular thin-film flow diverters with a lower percent metal coverage of 10-15% and 50-100 pores/mm$^2$ are also superior to conventional intrasaccular flow diverters having a percent metal coverage of 35% and 14 pores/mm$^2$.

Figure 12A:
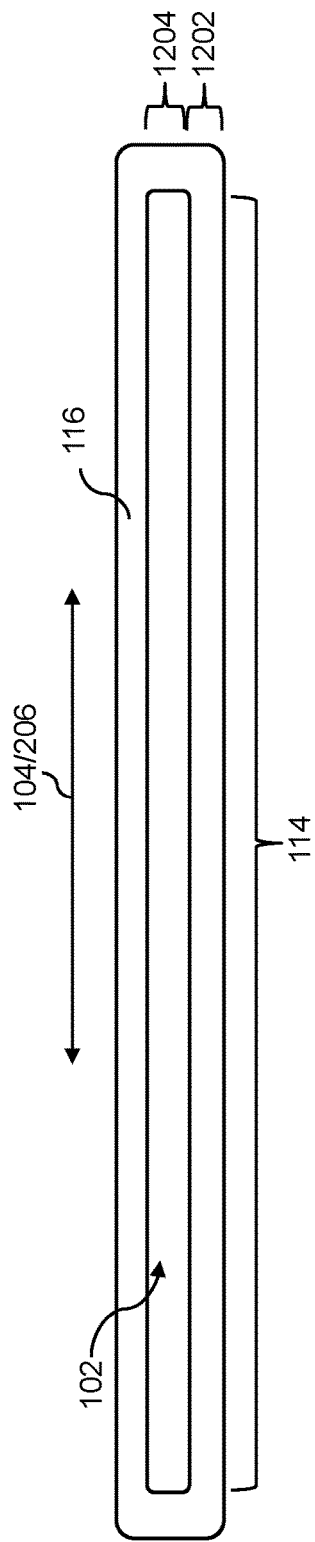
FIGS. 12A and 12B illustrate a fenestration of a thin-film mesh before and after expansion according to an embodiment of the present disclosure.
Figure 12B:
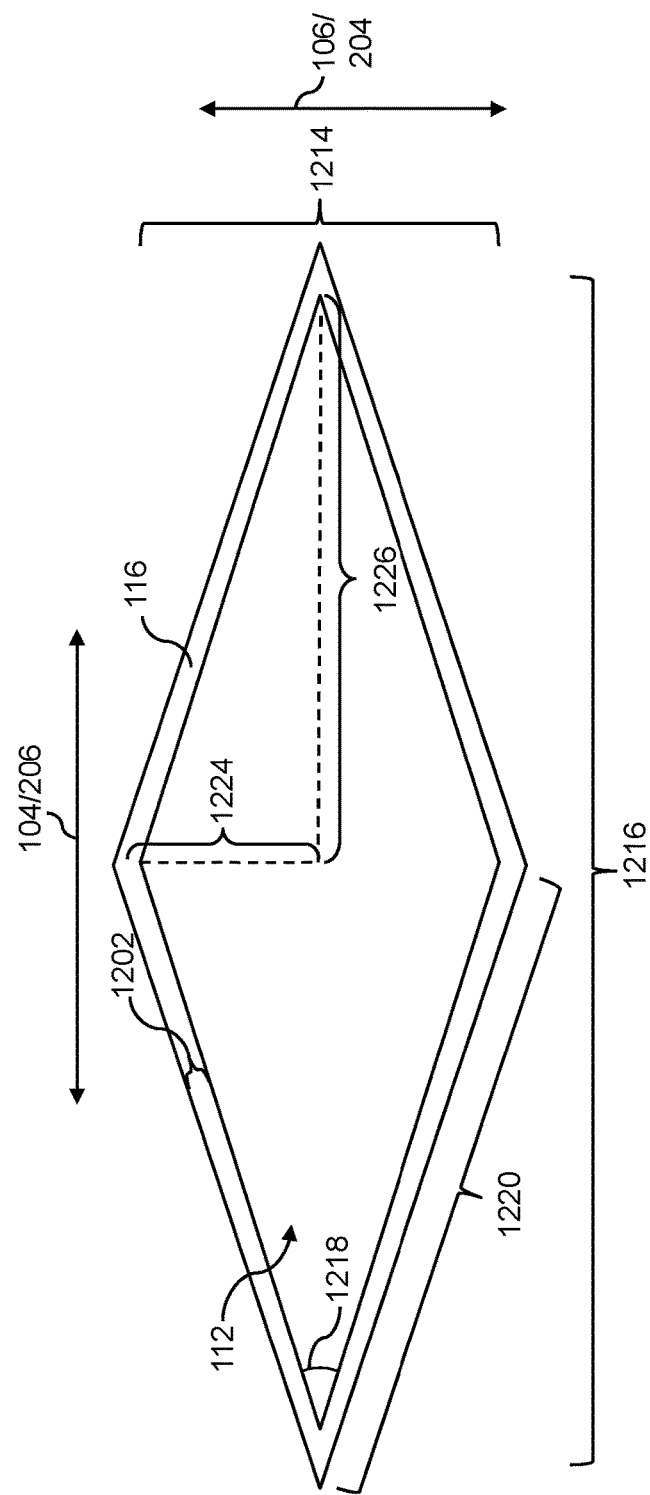

FIGS. 12A and 12B illustrate a fenestration of a thin-film mesh before and after expansion. FIG. 12A illustrates slit 102 (e.g., a closed fenestration) and struts 116 of thin-film mesh 100a surrounding slit 102 before expansion. Slits 102 may be oriented parallel to axis 104 of FIGS. 1A, 1B, and 1C or axis 206 of FIGS. 2A, 2B, and 2C. Strut 116, also referred to as surrounding portion 116, may have a strut width 1202, which may be between 1 and 25 µm. Slit 102 may have a slit width 1204 and a slit length 114. One half of slit width 1204 may be referred to as $Y_1$, and one half of slit length 114 may be referred to as $X_1$.

FIG. 12B illustrates pore 102 (e.g., an open fenestration) and surrounding portion/strut 116 of thin-film mesh 100b after expansion. Surrounding portion/strut 116 may have strut width 1202, which may be between 1 and 25 µm. Diamond-shaped pore 112 may have a short diagonal length 1214 along short diagonal axis (e.g., axis 106 of FIGS. 1A, 1B, and 1C or axis 204 of FIGS. 2A, 2B, and 2C), a long diagonal length 1216 along long diagonal axis (e.g., axis 104 of FIGS. 1A, 1B, and 1C or axis 206 of FIGS. 2A, 2B, and 2C), and a side length 1220. Diamond-shaped pore 112 may further have a strut angle θ 1218. In some embodiments, strut angle θ 1218 may be between 30 and 90 degrees. Length 1224, which is one half of short diagonal length 1214, may be referred to as $Y_2$, and length 1226, which is one half of long diagonal length 1216, may be referred to as $X_2$.

As side length 1220 is equal or approximately equal (e.g., slightly larger due to elongation of Nitinol thin-film mesh) to half of slit length 114 in FIG. 12A (given that pore 112 opens up from slit 102), side length 1220 may equal or be approximated as $X_1$. The lengths $X_1$, $X_2$, and $Y_2$, and strut angle θ may be related by the following equations:

$$\cos\frac{\theta}{2} = \frac{X_2}{X_1}$$

$$\sin\frac{\theta}{2} = \frac{Y_2}{X_1}$$

Accordingly, a percentage change in X (along axis 106/204) and a percentage change in Y (along axis 104/206) may be calculated. For example, if slit length 114 is 150 μm and slit width 1204 is 10 μm, and strut angle θ 1218 is 45°, then: $X_1$=75 μm, $Y_1$=5 μm, $X_2$=69.3 μm, $Y_2$=28.7 μm. The percent change in X is small, −7.6%, when compared to the percent change in Y, 474%.

For thin-film mesh 100*a* of FIG. 1A, the longitudinal length of thin-film mesh 100*a* (length along axis 104) will decrease by 7.6% when expanded along axis 106 to form thin-film mesh 100*b* of FIGS. 1B and 1C. For thin-film mesh 100*a* of FIG. 2A, the width of thin-film mesh 100*a* (length along axis 206) will decrease by 7.6% when expanded along axis 204 to form thin-film mesh 100*b* of FIGS. 2B and 2C. The circumference of cylindrical thin-film mesh 100*b* of FIGS. 2B and 2C may be 7.6% smaller than twice the width of thin-film mesh 100*a* in FIG. 2A accounting for the two layers of thin-film mesh 100.

Further, other features of diamond-shaped pores 112 may be determined by the following equations:

$$\text{Pore area} = 2X_2 Y_2$$

$$\text{Pore area with strut metal} = 2(X_2 + W)(Y_2 + W)$$

$$\text{Pore density} = \frac{1}{2(X_2 + W)(Y_2 + W)}$$

$$\text{Percent metal coverage} = 1 - \frac{2X_2 Y_2}{2(X_2 + W)(Y_2 + W)}$$

For example, if slit length 114 is 150 μm, slit width 1204 is 10 μm, strut width 1202 is 8 μm, and strut angle θ 1218 is 30°, then: $X_1$=75 μm, $Y_1$=5 μm, $X_2$=72 μm $Y_2$=19 μm, pore area=0.0027 $mm^2$, pore area with strut metal=0.0043 $mm^2$, pore density=230 pores/$mm^2$, and percent metal coverage=37%.

Figure 13B:
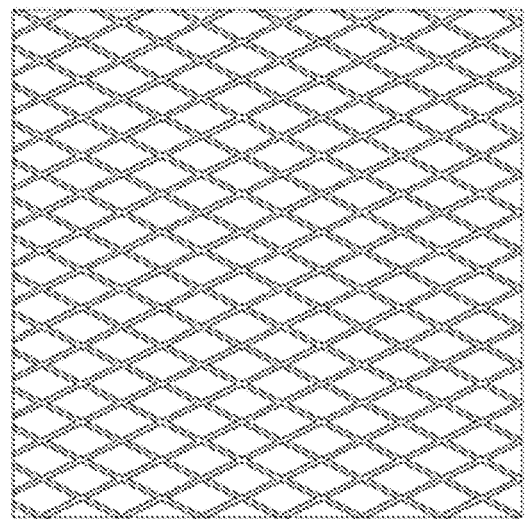
FIGS. 13A and 13B are diagrammatic top plan views of portions of thin-film meshes of thin-film covered devices according to various embodiments of the present disclosure.
Figure 13A:
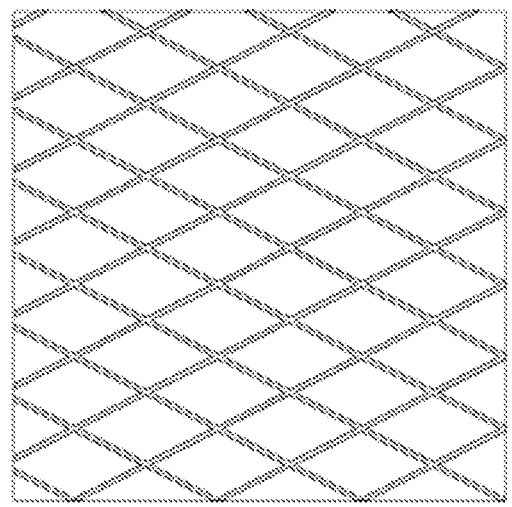

FIGS. 13A, 13B, and 13C show plan views of portions of thin-film meshes 100 with different percent metal coverage and pore densities. As shown in FIG. 13A, thin-film mesh 100*b* may have a pore density of between 38 pores/$mm^2$ and 70 pores/$mm^2$ with a strut angle of between 30 degrees and 90 degrees, a percent metal coverage of between 14% and 21%, and an edge density of between 23 mm of edge per $mm^2$ of surface area and 42 mm of edge per $mm^2$ of surface area. Thin-film mesh 100*b* may be fabricated as thin-film mesh 100*a* (not shown) with slit length 114 of between 225 μm and 400 μm (e.g., 300 μm). As shown in FIG. 13B, thin-film mesh 100*b* may have a pore density of between 134 pores/$mm^2$ and 227 pores/$mm^2$ with a strut angle of between 30 degrees and 90 degrees, a percent metal coverage of between 24% and 36%, and an edge density of between 40 mm of edge per $mm^2$ of surface area and 68 mm of edge per $mm^2$ of surface area. Thin-film mesh 100*b* may be fabricated as thin-film mesh 100*a* (not shown) with slit length 114 of between 50 μm and 200 μm (e.g., 150 μm).

An intrasaccular flow diverter covered with thin-film mesh 100*b* of FIG. 13A or FIG. 13B advantageously facilitates rapid and optimal healing of tissue defects such as aneurysms when compared to conventional intrasaccular medical devices. Further, compared to an intrasaccular flow diverter covered with thin-film mesh 100*b* of FIG. 13A, an intrasaccular flow diverter covered with thin-film mesh 100*b* of FIG. 13B may facilitate significantly more rapid and optimal healing due to the higher pore density and lower percent metal coverage. It will be appreciated that other percent metal coverage and pore density amounts may be used in further embodiments.

Figure 14B:
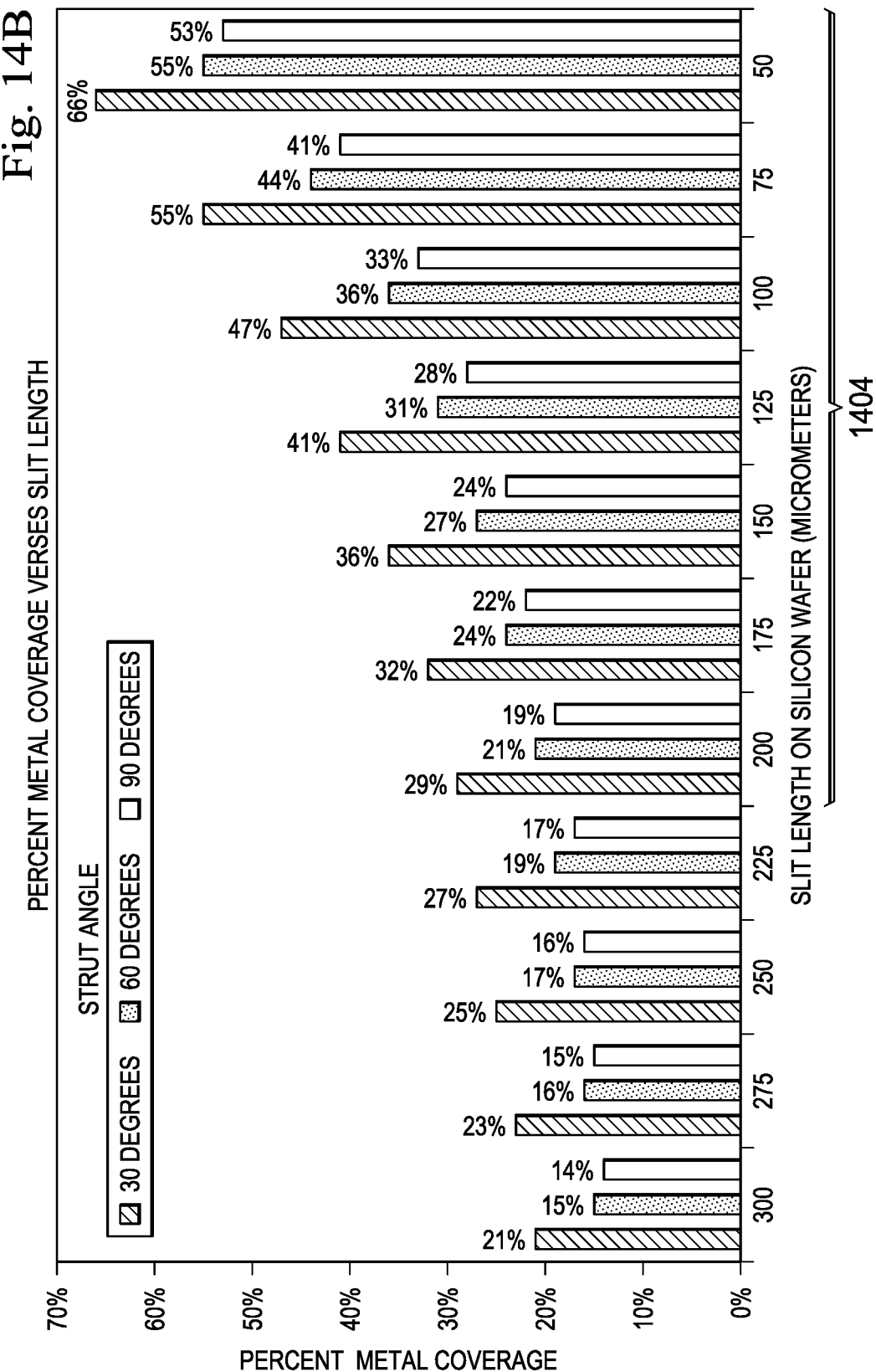

FIGS. 14A, 14B, and 14C are graphs characterizing thin-film meshes 100 when one or more physical characteristics are varied. FIG. 14A shows a graph of pore density vs. slit length 114, assuming strut width 1202 of approximately 8 μm. FIG. 14B shows a graph of percent metal coverage vs. slit length 114, assuming strut width 1202 of approximately 8 μm. FIG. 14C shows a graph of edge density vs. slit length 114, assuming strut width 1202 of approximately 8 μm. The ranges of the physical characteristics 1402, 1404, and 1406 that provide thin-film mesh 100 with advantageous properties including rapid fibrin deposition and cell growth (e.g., endothelialization) are shown in FIGS. 14A, 14B, and 14C.

Embodiments described herein illustrate but do not limit the invention. It should also be understood that numerous modifications and variations are possible in accordance with the principles of the present disclosure. Accordingly, the scope of the invention is best defined only by the following claims.

What is claimed is:

1. An apparatus, comprising:
   a device body comprising:
      a wire structure comprising a plurality of wires,
      a thin-film mesh placed over a length of the wire structure, and
      a plurality of crimps configured to secure the thin-film mesh to the wire structure at corresponding crimp locations,
   wherein a respective part of the wire structure and a respective part of the thin-film mesh between two adjacent crimps are configured to expand radially to form a thin-film covered spheroid spring, and wherein expanded parts of the thin-film mesh comprises pores;
   a first umbrella structure at a proximal end of the wire structure; and
   a second umbrella structure at a distal end of the wire structure.

2. The apparatus of claim 1, wherein the thin-film covered spheroid spring pushes the first umbrella structure and the second umbrella structure outwardly when compressed.

3. The apparatus of claim 1, wherein the wire structure comprises a braided wire or a laser-cut hypotube, and wherein the first umbrella structure comprises a braided wire or a laser-cut hypotube.

4. The apparatus of claim 1, wherein the thin-film mesh is a thin-film Nitinol (TFN) micromesh having a thickness of between 1 and 50 micrometers.

5. The apparatus of claim 1, wherein the thin-film mesh comprises slits having a length between 50 and 200 micrometers prior to expansion, wherein the slits open up to a corresponding diamond-shaped pore in response to expansion, and wherein the expanded thin-film mesh forms struts having a width between 1 to 25 micrometers around each pore.

6. The apparatus of claim 1, wherein the pore density of the expanded thin-film mesh is between 81 and 1075 pore per mm$^2$, and wherein the percent metal coverage of the expanded thin-film mesh is between 19 and 66%.

7. The apparatus of claim 1, wherein the spheroid spring comprises a spherical spring or an oval spring.

8. The apparatus of claim 1, wherein the device body is formed from a braided wire, and the first and second umbrella structures are formed from laser-cut hypotubes.

9. The apparatus of claim 1, wherein the device body, the first umbrella structure, and the second umbrella structure are formed from a single braided wire.

10. The apparatus of claim 1, wherein the device body, the first umbrella structure, and the second umbrella structure are formed from a single hypotube structure.

11. An apparatus, comprising:
a wire structure comprising a plurality of wires and a plurality of crimps provided along the wire structure at corresponding crimp locations, wherein a respective part of the wire structure between two adjacent crimps is configured to expand radially to form a spheroid spring;
a thin-film covered umbrella structure at a proximal end of the wire structure comprising umbrella struts and a thin-film sheet attached to the umbrella struts; and
another umbrella structure at a distal end of the wire structure.

12. The apparatus of claim 11, wherein the wire structure comprises a braided wire or a laser-cut hypotube, and wherein the umbrella struts comprise a braided wire or a laser-cut hypotube.

13. The apparatus of claim 11, wherein the thin-film sheet is a thin-film Nitinol (TFN) sheet having a thickness of between 1 and 50 micrometers.

14. The apparatus of claim 11, wherein the thin-film sheet is a thin-film mesh comprising pores.

15. The apparatus of claim 14, wherein the thin-film mesh comprises slits having a length between 50 and 200 micrometers prior to expansion, wherein the slits open up to a corresponding diamond-shaped pore in response to expansion, and wherein the expanded thin-film mesh forms struts having a width between 1 to 25 micrometers around each pore.

16. The apparatus of claim 14, wherein the pore density of the thin-film mesh is between 81 and 1075 pore per mm$^2$, and wherein the percent metal coverage of the thin-film mesh is between 19 and 66%.

17. The apparatus of claim 11, wherein the spheroid spring comprises a spherical spring or an oval spring.

18. The apparatus of claim 11, wherein the wire structure is formed from a braided wire, and the thin-film covered umbrella structure and the another umbrella structure are formed from laser-cut hypotubes.

19. The apparatus of claim 11, wherein the wire structure, the thin-film covered umbrella structure, and the another umbrella structure are formed from a single braided wire.

20. The apparatus of claim 11, wherein the wire structure, the thin-film covered umbrella structure, and the another umbrella structure are formed from a single hypotube structure.

* * * * *